United States Patent
Riisager et al.

(10) Patent No.: US 10,246,477 B2
(45) Date of Patent: Apr. 2, 2019

(54) ISOMERISATION OF C4-C6 ALDOSES WITH ZEOLITES

(71) Applicant: DANMARKS TEKNISKE UNIVERSITET, Kgs. Lyngby (DK)

(72) Inventors: Anders Riisager, Taastrup (DK); Shunmugavel Saravanamurugan, Kgs. Lyngby (DK)

(73) Assignee: DANMARKS TEKNISKE UNIVERSITET, Kgs. Lyngby (DK)

( * ) Notice: Subject to any disclaimer, the term of this patent is extended or adjusted under 35 U.S.C. 154(b) by 375 days.

(21) Appl. No.: 14/425,182

(22) PCT Filed: Sep. 3, 2013

(86) PCT No.: PCT/EP2013/068136
§ 371 (c)(1),
(2) Date: Mar. 2, 2015

(87) PCT Pub. No.: WO2014/033311
PCT Pub. Date: Mar. 6, 2014

(65) Prior Publication Data
US 2015/0232498 A1 Aug. 20, 2015

(30) Foreign Application Priority Data

Sep. 3, 2012 (DK) .............................. 2012 70530
Dec. 21, 2012 (EP) .................................. 12199009

(51) Int. Cl.
*C07H 3/02* (2006.01)
*C07H 1/00* (2006.01)

(52) U.S. Cl.
CPC ............... *C07H 3/02* (2013.01); *C07H 1/00* (2013.01)

(58) Field of Classification Search
CPC .................................... C07H 1/00; C07H 3/02
USPC ........................................................ 536/125
See application file for complete search history.

(56) References Cited

FOREIGN PATENT DOCUMENTS

WO       2012050625 A2    4/2012

OTHER PUBLICATIONS

Saravanamurugan et al, Catalysis Communications, 2012, 17, 71-75; online Oct. 12, 2011.*
Corma et al, Journal of Catalysis, 1996, 161, 713-719.*
Smith, J.G., Organic Chemistry, 3rd Ed., McGraw Hill, 2011, p. 1044.*
Rauter et al, Advances in Carbohydrate Chemistry and Biochemistry, 2010. pp. 1 and 69-70.*
Corma, Chem. Rev. 1995, 95(3), 559-614.*
Saravanannurugan et al, Catalysis Communications, 2012, 17, 71-75.*
Moreau, Claude et al., "Isomerication of glucose into fructose in the presence of cation-exchanged zeolites and hydrotalcites," Applied Catalysis A: General, vol. 193, 2000, pp. 257-264.
International Search Report for International Application No. PCT/EP2013/068136, dated Sep. 26, 2013, 3 pages.
Written Opinion of the International Searching Authority for International Application No. PCT/EP2013/068136, dated Sep. 26, 2013, 5 pages.

* cited by examiner

*Primary Examiner* — Ganapathy Krishnan
(74) *Attorney, Agent, or Firm* — Michael Best & Friedrich LLP

(57) ABSTRACT

The present invention relates to isomerization of C4-C6 aldoses to their corresponding C4-C6 ketoses. In particular, the invention concerns isomerization of C4-C6 aldoses over solid zeolite catalysts free of any metals other than aluminum, in the presence of suitable solvent(s) at suitable elevated temperatures. C6 and C5 aldose sugars such as glucose and xylose, which are available in large amounts from biomass precursors, are isomerized to fructose and xylulose respectively, in a one or two-step process over inexpensive commercially available zeolite catalysts, containing aluminum as the only metal in the catalyst. The ketoses obtained are used as sweeteners in the food and/or brewery industry, or treated to obtain downstream platform chemicals such as lactic acid, HMF, levulinic acid, furfural, MMHB, and the like.

19 Claims, 11 Drawing Sheets

ISOMERISATION OF C4-C6 ALDOSES WITH ZEOLITES

CROSS-REFERENCE TO RELATED APPLICATIONS

Figure 1:
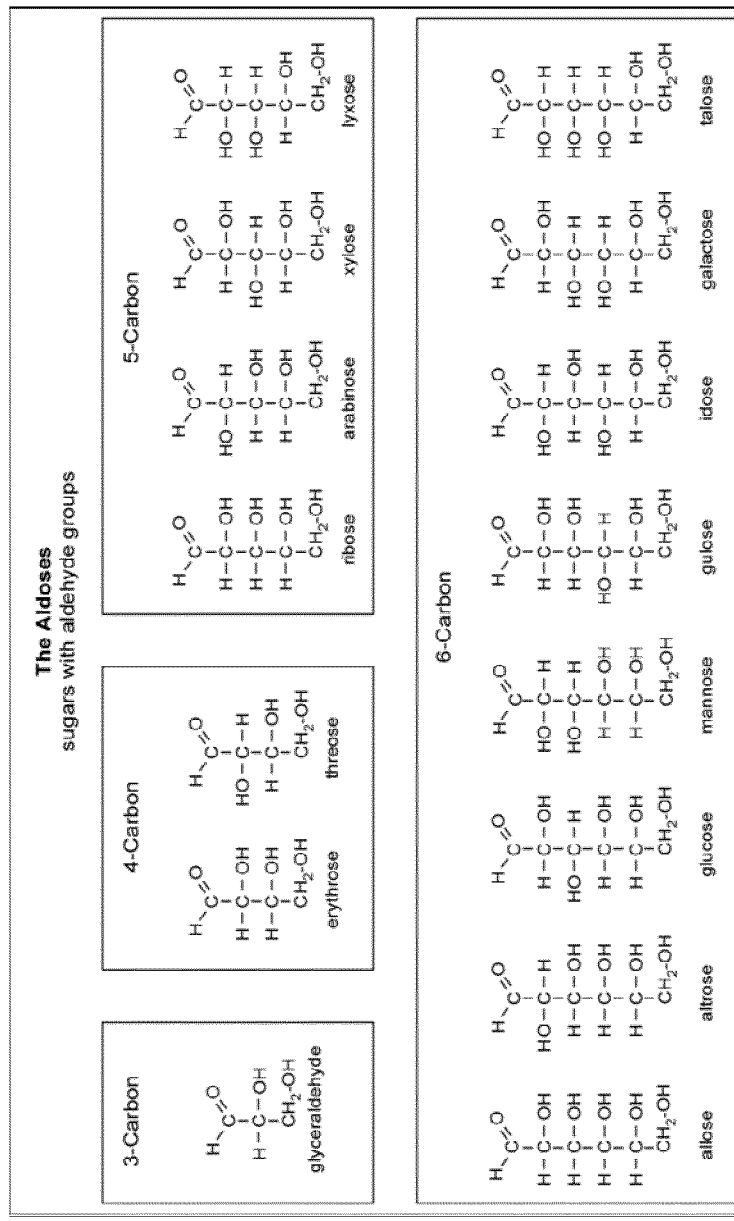

This is a U.S. national stage entry of International Patent Application No. PCT/EP2013/068136, filed on Sep. 3, 2013, which claims priority to European Patent Application No. 12199009.7, filed on Dec. 21, 2012 and Denmark Patent Application No. PA 2012 70530 3, filed on Sep. 3, 2012, the entire contents of all of which are fully incorporated herein by reference.

The present invention relates to isomerization of C4-C6 aldoses to their corresponding C4-C6 ketoses. In particular, the invention concerns isomerization of C4-C6 aldoses over solid zeolite catalysts free of any metals other than aluminum, in the presence of suitable solvent(s) at suitable elevated temperatures. C6 and C5 aldose sugars such as glucose and xylose, available in large amounts from biomass precursors, are isomerized to fructose and xylulose respectively, in a two-step one-pot process over inexpensive commercially available zeolite catalysts, containing aluminum as the only metal in the catalyst.

BACKGROUND

Fructose is an isomer of the hexose (C6) aldose sugars glucose and mannose. Glucose is the most abundant monosaccharide in nature and the cheapest hexose. Cellulose as the structural component of the primary cell wall of green plants and many forms of algae consists of a linear chain of several hundred to over ten thousand β(1→4) linked D-glucose units and therefore a unlimited source of glucose for isomerization to fructose. Fructose is widely used in the food industry as sweetener (high-fructose corn syrup, HFCS), since it contributes many useful physical and functional attributes to food and beverage applications. On the other hand, one attractive approach to convert biomass into biofuels and feedstock chemicals is the direct conversion of hexose carbohydrates into 5-hydroxymethylfurfural (HMF) and/or levulinic acid in aqueous media or levulinate esters in the presence of an alcohol. In contrast to glucose, fructose readily dehydrates to form HMF using an acid catalyst followed by the etherification with an alcohol.

Traditionally, the equilibrium limited isomerization of glucose to fructose has been carried out industrially in the presence of the enzyme glucose/xylose isomerase. To achieve high enzyme specificity without formation of side products the reaction requires ambient pH conditions and temperature. However, from an economic point of view, the activity of enzymes is still low and large quantity of enzyme is thus needed. Moreover, irreversible deactivation of the enzyme may occur. Recently, a combined use of ultrasound irradiation and ionic liquids has been studied by Wang et al. (Wang, Y.; Pan, Y.; Zhang, Z.; Sun, R.; Fang, X.; Yu, D. Process Biochemistry 2012, 47, 976) to improve the reaction rate and product yield in enzymatic isomerization of glucose to fructose allowing achieving a fructose yield of 45.3%.

Alternatively to enzymes, glucose can be transformed into fructose by aldose-ketose isomerization, in the presence of a base. However, the monosaccharides are unstable in alkaline media and a high amount of by-products are produced due to side reactions. Generally, Brnsted acids are not efficient catalysts for aldose isomerization, although the efficacy may be a function of reaction conditions (Kruger, J. S.; Nikolakis, V.; Vlachos, D. G. Current Opinion in Chemical Engineering).

Xylulose is an isomer of the pentose (C5) sugar xylose. Xylose is a precursor of hemicellulose, which comprises about 30% of plant matter. Wood and other plant materials provide unlimited sources of xylose and its precursors. Another 45% of the plant material is cellulose, 15% are lignin and about 10% are ash. Xylulose may be used as a chemical platform for different enzymatic or chemical processes or converted, e.g. by fermentation to ethanol and used as biofuel. Apart from this, xylulose is an intermediate to form furfural from xylose. Furfural is one of the important platform chemicals, which can be used to produce a verity of chemicals such as furfural alcohol, 2-methyl furan, furan, tetrahydrofuran, furfuryl amine, etc.

Among solid acid catalysts, zeolites have widely been used in the petroleum industry because of the many advantages they present. As heterogeneous catalysts, zeolites do not require costly post-reaction separation processes that are needed for many homogeneous catalysts, and they can be used under a wider range of reaction conditions than biocatalysts.

Zeolites are tridimensional crystalline aluminosilicates with the following formula in the as-synthesized form: $xM_{2/n}O \cdot xAl_2O_3 \cdot ySiO_2 \cdot WH_2O$ where M is a cation which can belong to the group IA or IIA or can be an organic cation, while n is the cation valence, and W represents water contained in the zeolite voids. Crystalline structures of the zeolite type but containing tetrahedrally coordinated Si, Al, P, as well as transition metals and many group elements with the valence ranging from I to V such as, Sn, B, Ga, Fe, Cr, Ti, V, Mn, Co, Zn, Cu, Sr, etc., have been synthesized with the generic name of zeotypes, including $AlPO_4$, SAPO, MeAPO, and MeAPSO type molecular sieves. The main characteristic of the zeolites and zeotypes is that the tetrahedral primary building blocks are linked through oxygen producing a three-dimensional network containing channels and cavities of molecular dimensions.

The channel sizes are conventionally defined as ultralarge pore materials (>12-membered rings) with a free diameter above 8 Å, large (12-membered rings) with a free diameter of about 6-8 Å, medium (10-membered rings) with a free diameter of about 4.5-6 Å, or small (8-membered rings) with a diameter of about 3-4.5 Å, depending on the smallest number of O, Al and Si atoms that limits the pore aperture of their largest channel. Examples of zeolites and zeotypes with different pore size may be found in Chemical Reviews, 95 (1995) 559-614. The system of channels in these molecular sieves produces solids with very high surface area and pore volume, which are capable of adsorbing great amounts of substrate/reactants. This fact combined with the possibility to generate active sites inside of the channels and cavities of zeolites and zeotypes produces a very unique type of catalyst, which by itself can be considered as a catalytic microreactor.

Zeolites containing tetravalent metal atoms in tetrahedral coordination modes have been explored as solid Lewis acid catalysts. Recent studies have shown that metal centers are highly active for the isomerization of glucose. In particular, the Lewis acid zeolite Sn-BEA has been shown effective for catalyzing the isomerization of a series of C5 and C6 sugars: dihydroxyacetone (DHA), glyceraldehyde, and glucose with activities comparable to biological processes by a mechanism similar to enzymatic catalysts (5-8). However, Sn-BEA is cumbersome to synthesize and incorporate tin metal, which is a toxic heavy metal and therefore potentially dangerous to the environment and down-stream products.

SUMMARY OF THE INVENTION

The present invention overcomes the drawbacks of the prior art by making it possible to isomerize C4-C6 sugars from their aldose forms to the corresponding 2-ketose forms by using a zeolite catalyst containing only aluminum as the only metal component ("Zeolite-Al"). Such catalysts may be inexpensive commercially available solid acidic zeolites, containing only aluminum in addition to silicon, oxygen and hydrogen ("Zeolite-Al"). Such commercial zeolites may be natural zeolites and may therefore contain trace amounts of other components, such as other metals, without these having any influence on the isomerization according to the present invention.

Commercial large-pore zeolites have been demonstrated to provide excellent catalytic performance in the isomerization of glucose and subsequent etherification in methanol. No equilibrium between the three sugar isomers glucose, fructose and mannose was detected in alcohol media, in contrast to what is found in water. The best result for formation of fructose was obtained using the zeolite H-USY (Lew, C. M.; Rajabbeigi, N.; Tsapatsis, M. Microporous and Mesoporous Materials 2012, 153, 55) with optimal levels of Brnsted and Lewis acidity (Si/Al ratio of 6).

The aldoses being converted by isomerization according to the present invention belongs to the group of monosaccharides, referred to as C6 sugars (C6 aldoses), for example glucose, which is isomerized to the corresponding C6 ketose, fructose, C5 sugars (C5 aldoses), for example xylose which is isomerized to the corresponding C5 ketose, xylulose and C4 sugars (C4 aldoses), for example erythrose, which is isomerized to the corresponding C4 ketose, erythrulose. The isomerization takes place over "Zeolite-Al" in a suitable solvent or combination of solvents at a suitable temperature in a one-step or two-step process. The two process steps in the two-step process may be performed in the same reaction chamber, a so-called one-pot process.

Isomerization of C4-C6 aldose may follow a one-step process, which takes place either in an aqueous or an alcoholic media at a suitable temperature between 60 and 140° C., using as a catalyst a solid acidic zeolite, containing aluminum as the sole metal component ("Zeolite-Al").

The yield in isomerization of C5 and C6 aldoses may be further enhanced by adding a second step, whereby the isomerization follows a two-step process using as a catalyst a solid acidic zeolite, containing aluminum as the sole metal component ("Zeolite-Al") at an elevated temperature in the range 60-140° C. In the first step, a suitable alcohol, e.g. methanol, is used, and in the second step an aqueous media, e.g. water, is used.

The catalyst could be reused in five consecutive reaction runs keeping the same initial activity. This clearly demonstrates the generality of the concept and enables potential new catalytic applications of zeolites with combined Brnsted and Lewis acid sites in reaction protocols, where sugar isomerization is favored at relatively low temperature and direct transformation to industrially importantly chemicals (e.g. levulinate esters) are facilitated at higher temperature. The similar approach has been applied for C5 sugars and the results reveal that xylose follow the same reaction pathway as described for glucose. It is a clear demonstrated that the presently disclosed reaction (pathway) can be applied for other sugar isomerization reactions. Furthermore, a catalyst that combines Brnsted and Lewis acid sites is a very promising catalyst since at low temperatures sugar isomerization is favored, while at higher temperatures glucose can be directly converted into levulinate esters, versatile chemical feedstock with numerous potential industrial applications. The isomerisation of the C4 sugars, erythrose to erythrulose has been done one step in water unlike C5 and C6 sugars isomerisation. It has been observed that H-USY-6 showed excellent catalytic activity which is higher than the other tested H-Y, H-beta, H-mordenite and H-ZSM-5 catalysts. The isomeristion of erythrose to erythrulose is an important step, for example because erythrulose can be converted into methyl-4-mthoxy-2-hydroxybutanoate (MMHB), which is precursor to make new polyesters.

FIGURES

Figure 2:
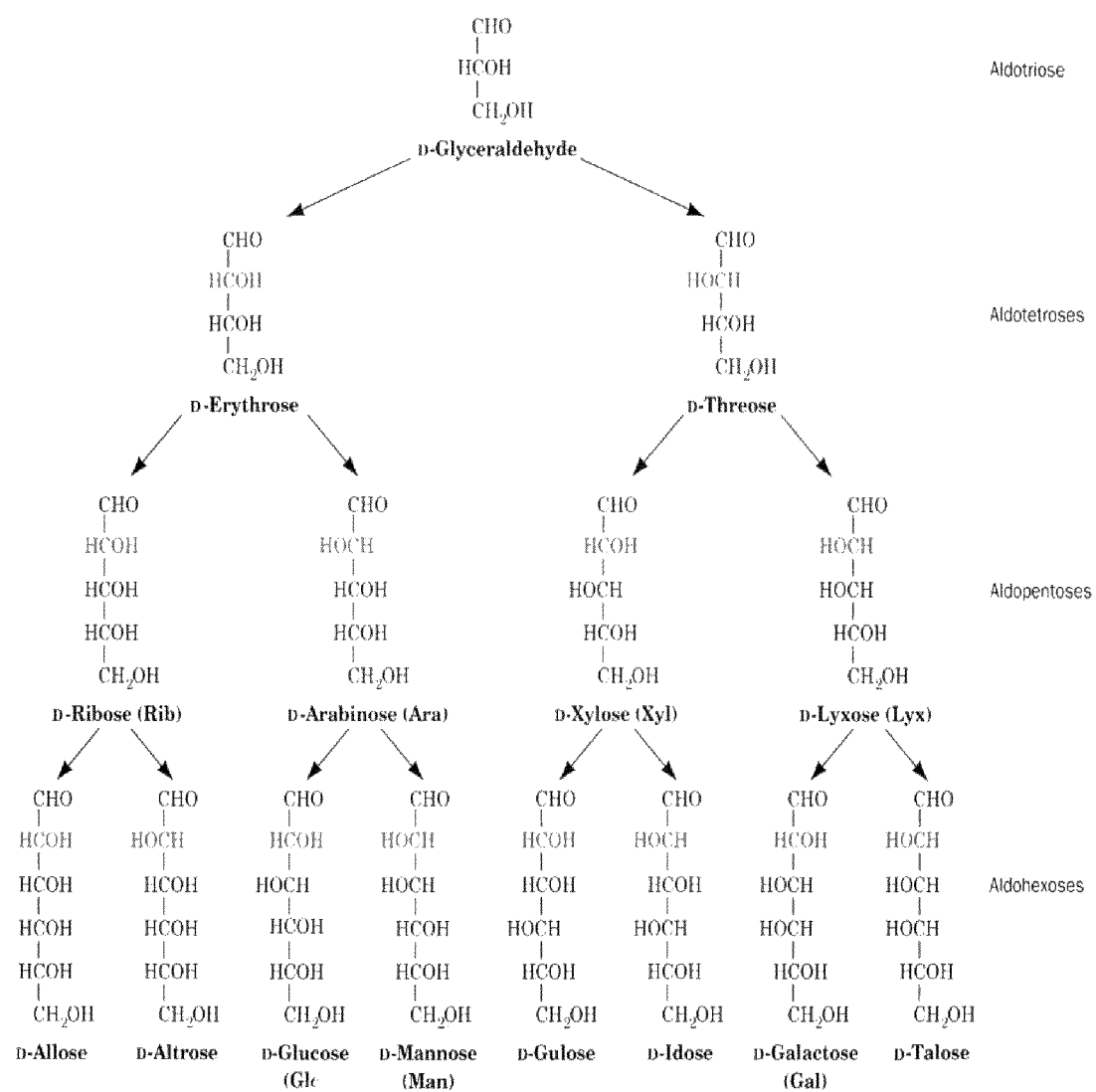
Figure 3:
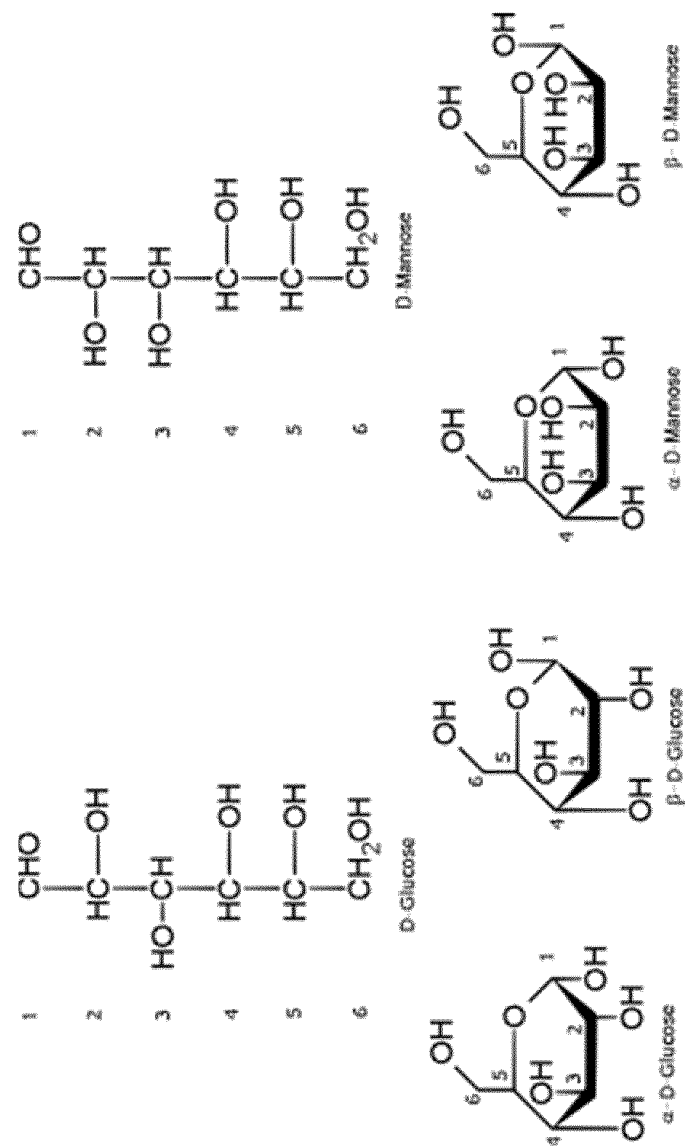
Figure 4:
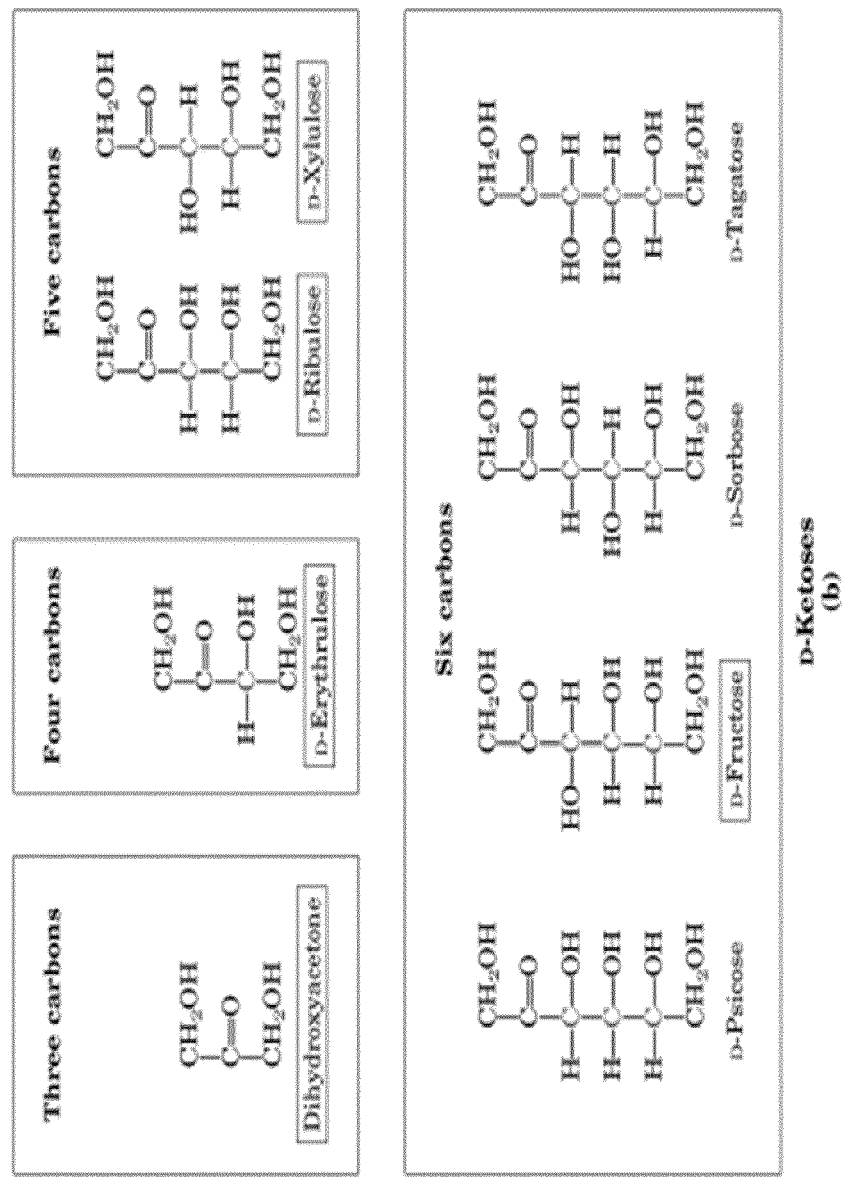
Figure 5:
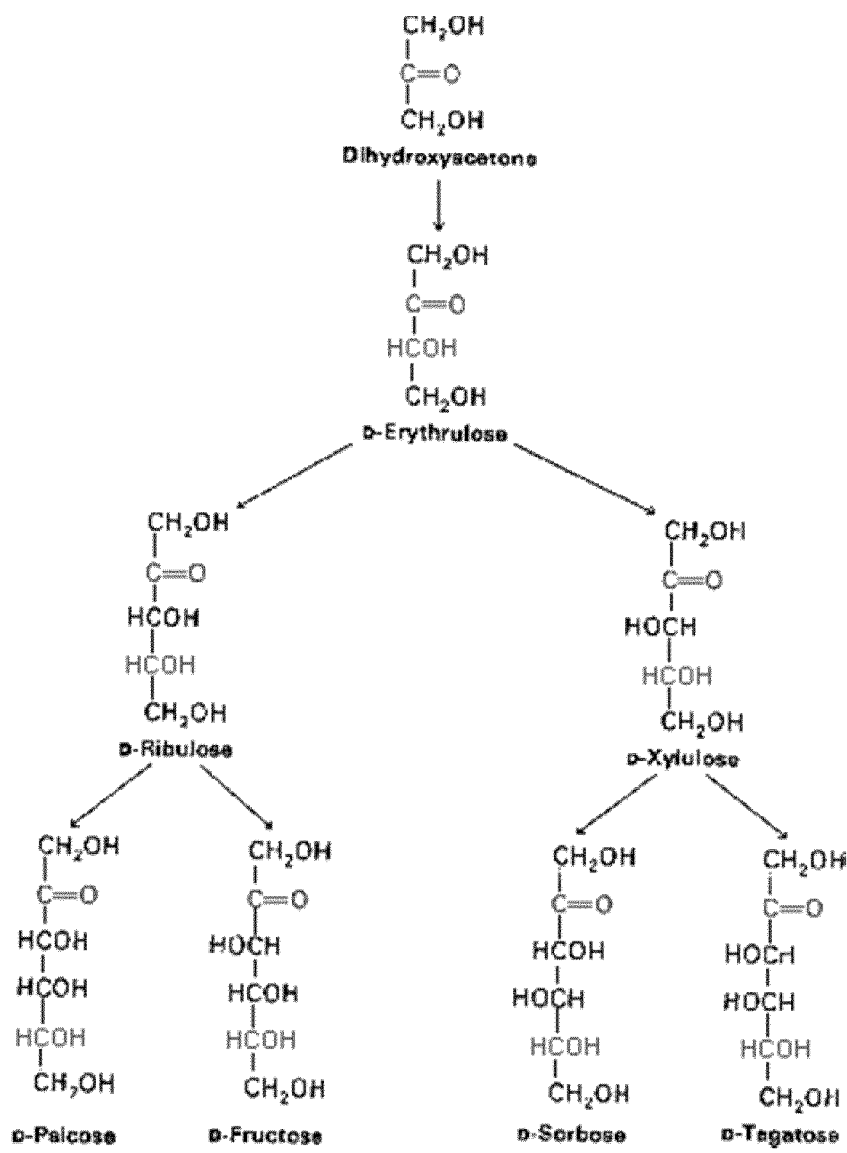
Figure 6:
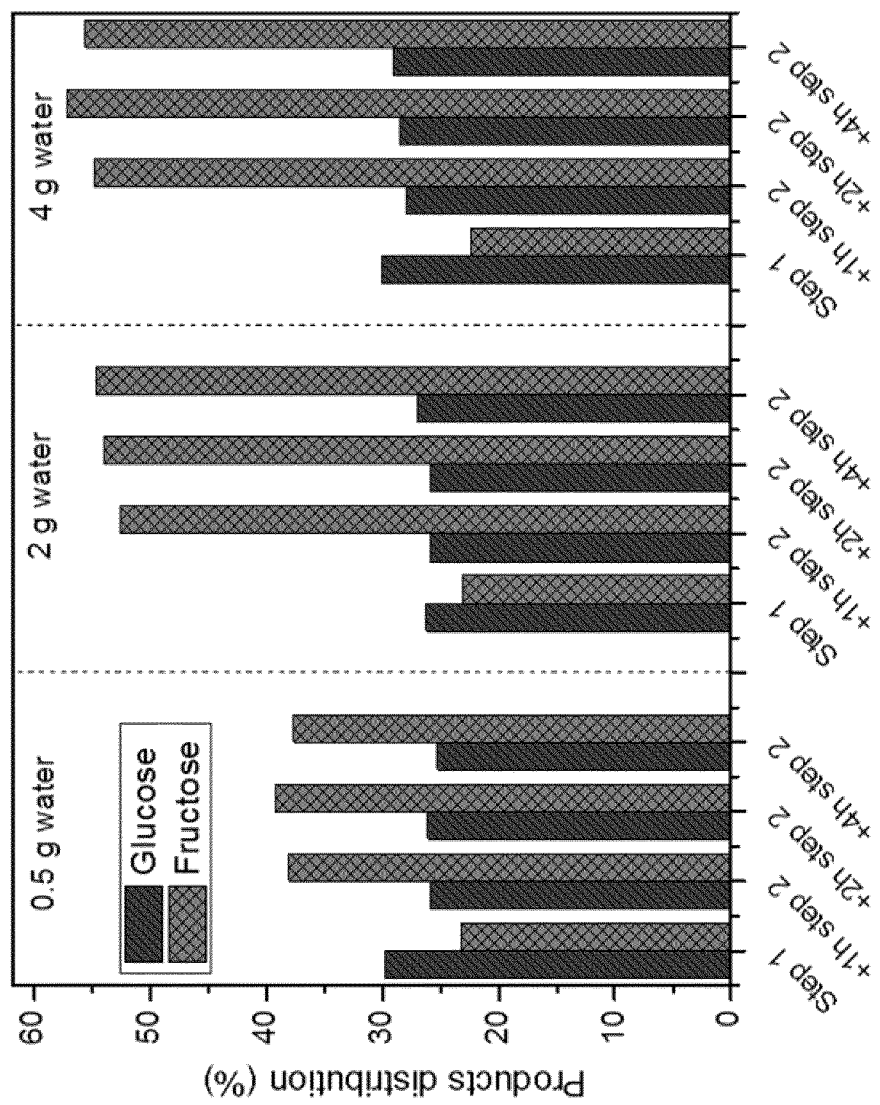

FIG. 1 shows a list of aldoses in Fischer projection.
FIG. 2 shows aldotetroses, aldopentoses and aldohexoses.
FIG. 3 shows the aldoseshexoses glucose and mannose.
FIG. 4 shows a list of ketoses in Fischer projection.
FIG. 5 shows ketotetrose, ketopentoses and ketohexoses.
FIG. 6 shows optimization of the amount of water added and the reaction time for the second step.

Reaction conditions: Step 1: 75 mg H-USY-6, 125 mg glucose, 4 g methanol, 1 h, 120° C.

Figure 7:
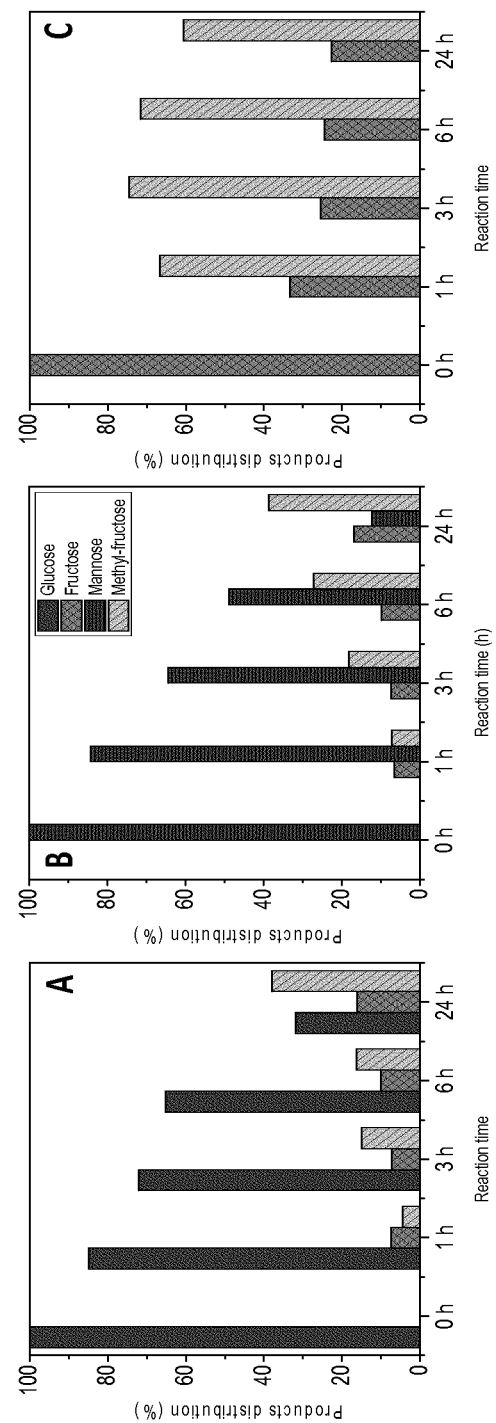

FIG. 7 Influence of reaction time on the products distribution over H-USY-6, starting from glucose (A), mannose (B) and fructose (C) at 80° C. Step 1: 75 mg H-USY-6, 125 mg sugar, 4 g methanol.

Figure 8:
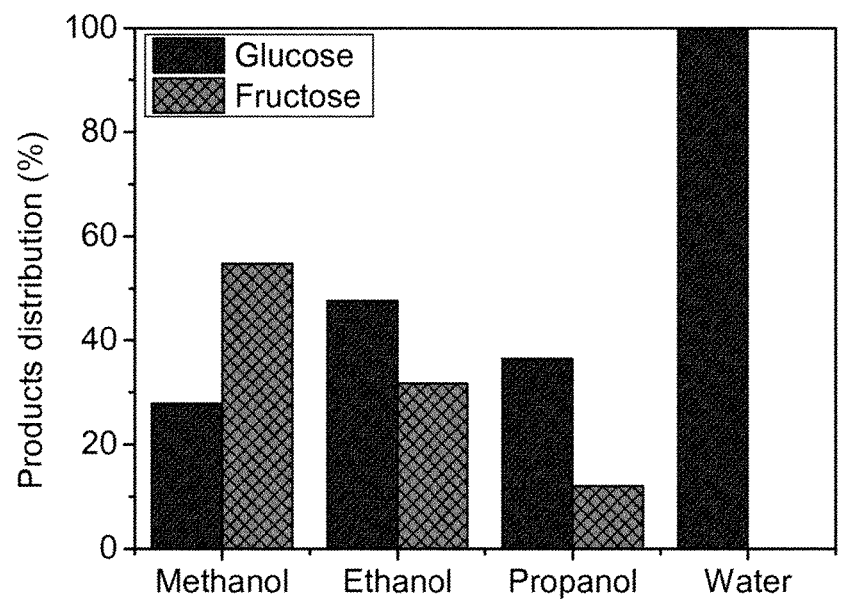

FIG. 8 shows a comparison of different solvents for the conversion of glucose. Step 1: 75 mg H-USY-6, 125 mg glucose, 4 g solvent, 1 h, 120° C.; Step 2: 4 g water, 1 h, 120° C.

Figure 9:
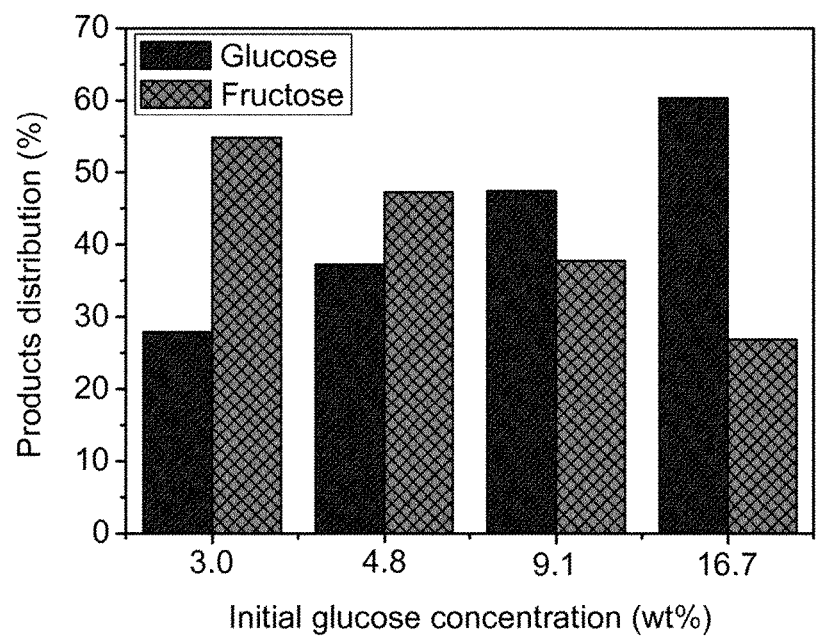

FIG. 9 shows the effect of initial glucose concentration for glucose conversion. Step 1: 75 mg catalyst, 4 g methanol, 1 h, 120° C.; Step 2: 4 g water, 1 h, 120° C.

Figure 10:
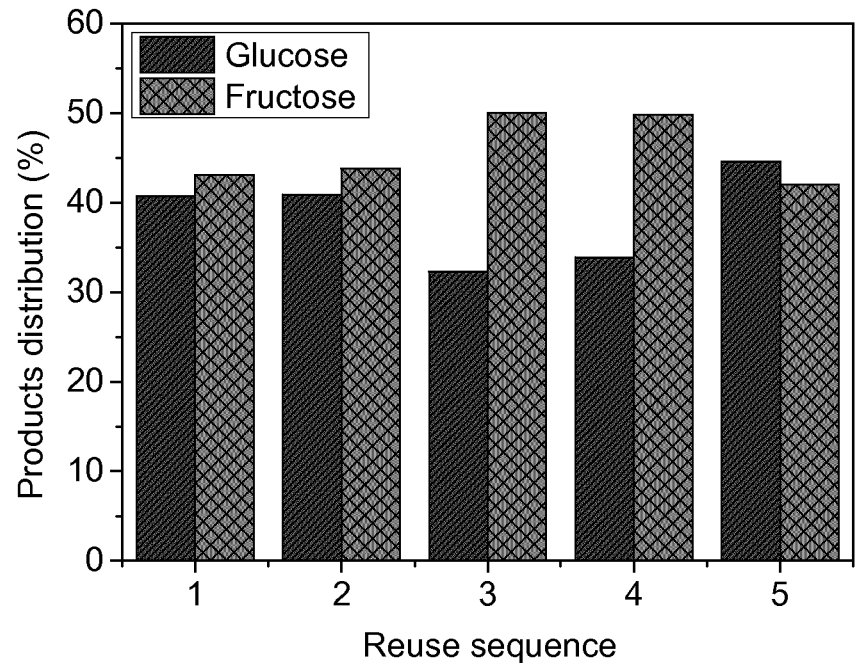

FIG. 10 shows reuse of H-USY (Si/Al=6) for glucose conversion. Step 1: mass ratio catalyst/glucose=0.6, 4 g methanol, 1 h, 120° C.; Step 2: 4 g water, 1 h, 120° C.

Figure 11:
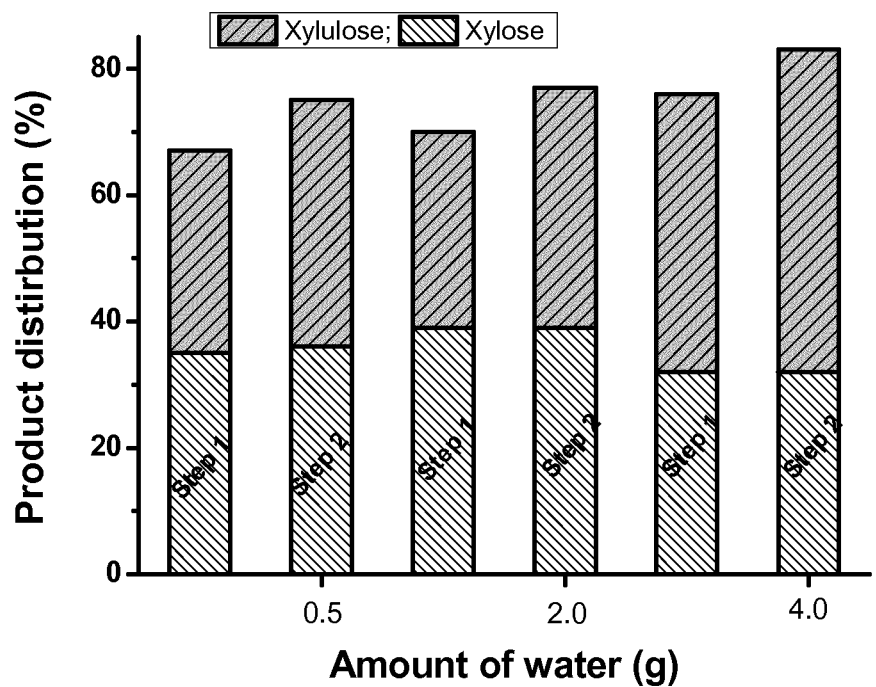

FIG. 11 shows the influence of water content during the second step for the conversion of xylose to xylulose. Step 1: 75 mg H-USY-6, 125 mg xylose, 4 g methanol, 1 h, 100° C.; Step 2: 1 h, 100° C.

Figure 12:
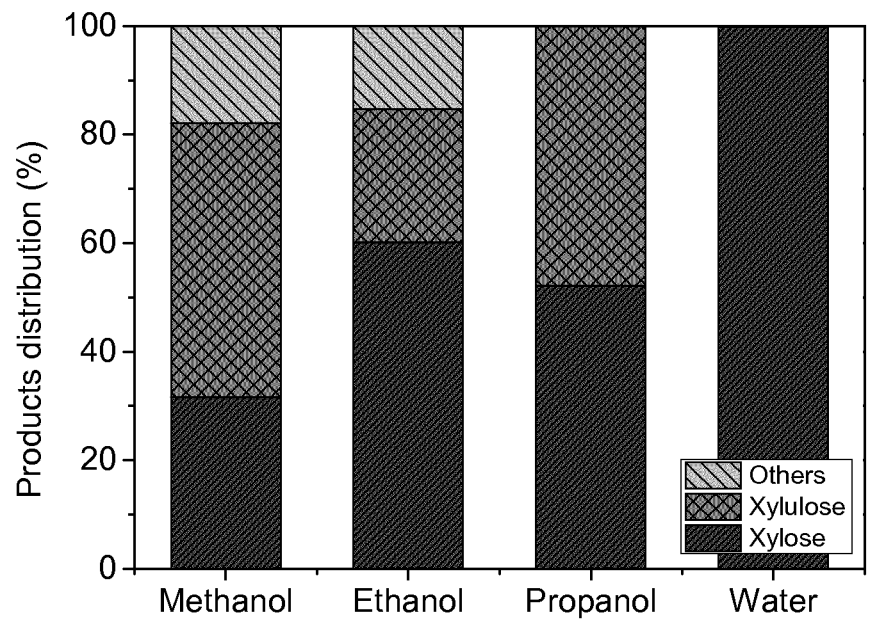

FIG. 12 shows a comparison of different solvents for the conversion of xylose after second step. Step 1: 75 mg H-USY-6, 125 mg xylose, 4 g solvent, 1 h, 100° C.; Step 2: 4 g water, 1 h, 100° C.

Figure 13:
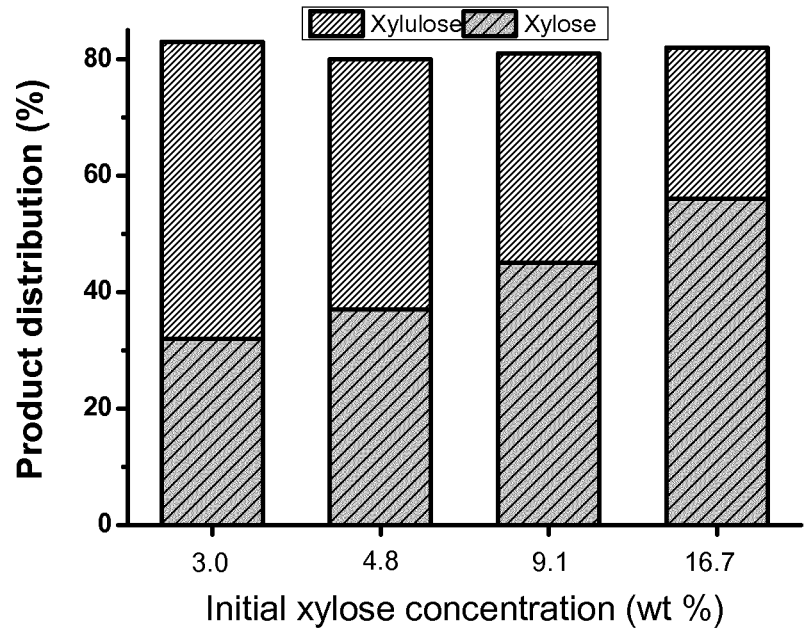

FIG. 13 shows the effect of the initial xylose concentration for xylose conversion after the second step.

Step 1: 75 mg H-USY-6, 4 g methanol, 1 h, 100° C.; Step 2: 4 g water, 1 h, 100° C.

Figure 14:
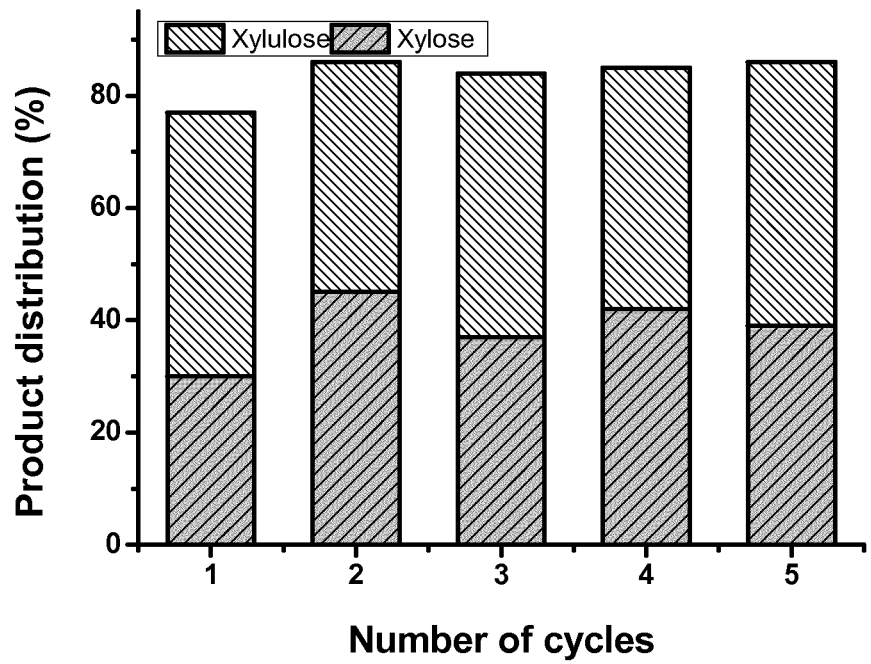

FIG. 14 shows reuse of H-USY-6 for xylose conversion after the second step.

Step 1: mass ratio catalyst/glucose=0.6, 4 g methanol, 1 h, 100° C.; Step 2: 4 g water, 1 h, 100° C.

Figure 15:
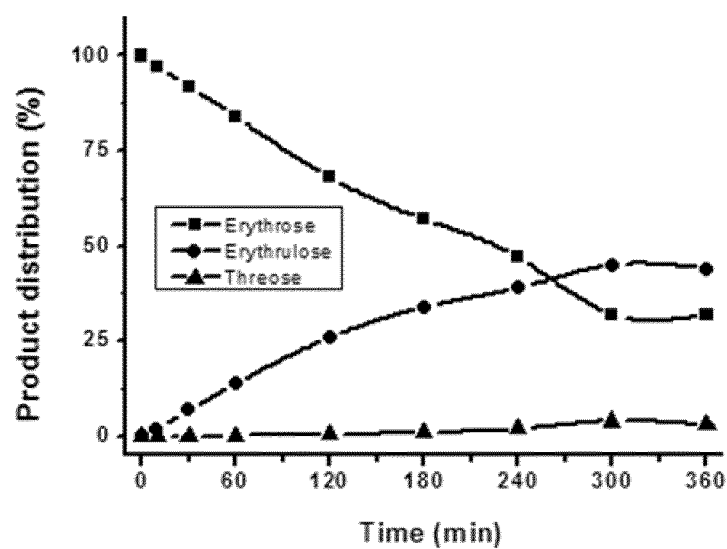

FIG. 15 shows the influence of reaction time on the product distribution of tetroses. Reaction Conditions: Erythrose=0.0632 g of 0.093M; H-USY-6=0.0375 g; Water=5.58 g; Temp.=120° C.

DETAILED DESCRIPTION

The present invention concerns a new pathway for isomerization of sugars of the aldoses type by use of solid catalysts substantially devoid of any other metal atoms than aluminum.

The group of catalysts with properties useful in the method according to the present invention is the so-called zeolites. In 2011, over 40 naturally occurring zeolite frameworks were known. In addition over 180 synthetic zeolites and zeotypes with different pore sizes and structures have been produced over the time. According to the present invention, only zeolites and zeotypes with large pores (by definition above 6 Å) and the right Si/Al ratio are efficient for use in the present method of isomerizing C4-C6 aldoses to their corresponding ketoses. This means that in practice, the pore size diameter should be more than 5 Å, preferable 6 Å or more. Table 1 shows examples of tested zeolites and their pore sizes.

Two commercially available acidic zeolite catalysts with large pores, H-Y (a fajusite (FAU) catalyst) and H-beta (a BEA catalyst) were shown to possess the desired properties. The present invention is however by no means limited to these two types of catalysts. Other zeolites with large pores (see Table 1) may be shown to possess the same desired properties and thus used as catalyst in a method according to the present invention. The skilled person would know have to identify such catalyst from the present teaching.

Fajusites

Fajusite zeolites (FAU) are divided into two types, X and Y. Y zeolites can be dehydrated and dealuminated to produce ultra-stable Y (USY) zeolites which are commercially available. Zeolite Y is classified under large pore zeolites since it has pore diameter of 7.4 Å. Zeolite Y has a 3-dimensional pore structure with pores running perpendicular to each other in the x, y, and z planes, and is made of secondary building units 4, 6, and 6-6. The pore diameter is as large as 7.4 Å since the aperture is defined by a 12 member oxygen ring, and leads into larger cavities of a diameter of 12 Å. The cavity is surrounded by ten sodalite cages (truncated octahedra) connected on their hexagonal faces. Commercially available Y (H-Y or HY) catalysts are often named H-VUSY (e.g. H-VUSY-6), H-SDUSY (e.g H-SDUSY-30) or H-USY, indicating specific preparations before use, for example steam treatment.

Beta Zeolites

Beta Zeolite (BEA; H-beta) is three-dimensional large-pore zeolites with a 12-membered ring system. Zeolite BEA is the only large-pore zeolite having chiral pore intersections. The pore structure of BEA consists of 12-membered rings interconnected by cages formed by the intersections of the channels. The channel system of zeolite Beta has pore diameters of about 7 Å, which are similar to other large-pore molecular catalysts such as FAU.

Si/Al Ratio

The adsorption characteristics of zeolites will allow discrimination between competing reactants and products by modifying their relative adsorption interaction, which can be done for example by changing the Si/Al ratios in the catalytic structures. This can be achieved by changing the Si/Al ratio by either synthesis or post synthesis treatments. For example, alkaline treatment of zeolites may lead to extensive silicon extraction at mild treatment conditions. This leads to a lower Si/Al ratio, but also impacts on the microporous and acidic properties of the resulting catalyst. As will become clear from the present invention, an optimal window of Si/Al ratios identified for one zeolite family does not necessary apply to other zeolite families. The optimal Si/Al window needs to be established for each zeolite family individually. Extraction of silicon may lead to substantial mesoporosity of the treated catalyst and presumably an improved transport of the reactants.

Acidity

In addition to pore size, the catalysts for use in the present method should have the right acidic properties. As discussed above, one way of securing, controlling and/or changing acidic properties is by selecting a catalyst with the right Si/Al ratio, i.e. Si/Al ratio window, or changing the ratio of other catalysts with less efficient structures. The complexity of the catalyst structures also leads to different acids sites with different strengths in a particular zeolite framework. It has turned out, that the two illustrative zeolites possess a "medium" (type 1) and a "strong" (type 2) acid site as measured by the $NH_3$-TPD method. A measure of the acidic properties of a certain catalyst for use in the present invention is thus the number of acidic sites and the ratio between type 1 and type 2 acid sites. Such a measure can be used to select possible useful catalysts for further testing.

The $NH_3$-TPD method is a conventional method that is extensively used to measure the acidity of solid catalysts (Chem. Rev., 1995, 95, 559-614). In the $NH_3$-TPD method, adsorption of volatile amines such as $NH_3$ are used to determine the number of acidic sites in a solid catalyst. $NH_3$ is absorbed on both Brnsted and Lewis sites if both types of acid sites are catalytically active. $NH_3$ chemically adsorbed on the catalyst is evacuated by thermal desorption (TPD) and the acid strength calculated according to the proportion evacuated at various temperatures. The two acid sited provide for a strong acid site (type 2) and a medium acid site (type 1), the adsorption being stronger at the strongest acid site, thus calling for a higher temperature for desorption. The number of acidic sites in some of the catalysts tested in a method according to the present invention has been measured according to the $NH_3$-TPD method (example 5) and the results are shown in Table 2.

The present invention thus concerns a new pathway to obtain high yields of C4-C6 ketoses from the corresponding aldose sugars, involving either a one-step process or a two-step process over a suitable solid acidic zeolite. For the C5 and C6 aldose sugars, a two-step process leads to a higher yield of the ketoses than the one-step process. The C4 aldose sugars are advantageously converted in a one-step process. The invention thus presents a new method for converting C4-C6 sugars from their aldose forms to the corresponding 2-ketose forms in high yields involving isomerization over a suitable catalyst, which catalyst contains aluminum as the only metal in its chemical structure, i.e. does not contain any other metal atoms, in particular tetravalent metals atoms, such as tin (Sn), titanium (Ti), zirconium (Zr), hafnium (Hf) and germanium (Ge). The present invention surprisingly results in high yields of C4-C6 ketoses in isomerization processes involving any C4-C6 aldose substrate, such as for example the cheap biomass precursors glucose and xylose, where the catalyst may be any cheap commercially available zeolite catalyst with the right properties. Thus, in addition to avoiding the use of catalysts comprising potentially toxic metals, the hassle and difficulties in producing "spiked" catalysts comprising other tetravalent metal atom than aluminum, the present invention is also favorable for economically reasons, as "spiked" catalysts are normally not commercially available and expensive to produce in higher amounts. Advantageously, the present invention allows the application of an inexpensive common commercially available solid zeolite catalyst, containing aluminum as the only metal component ("Zeolite-Al") in an isomerization process converting aldoses to ketoses. Zeolites containing aluminum as the only metal are found in the nature. They may also be produced relatively easy in the laboratory.

The temperatures applied in a two-step reaction is the same or different in the two steps, and is from about 60° C. to an upper limit governed by the melting temperatures of the aldose/ketose and practical considerations such as undesirable high pressure in the reaction chamber due to evaporation of the solvents and other handling properties. The same applies to the temperature in the one-step-reaction. Thus, the temperature in each step is 60° C. or more, 80° C. or more, 100° C. or more, 110° C. or more, 120° C. or more, 130° C. or more, 140° C. or more, or even higher. It is realized that the selected temperature governs the time needed in each heating step. The higher the temperature, the shorter the heating time and vice versa. Heating time (reaction time) may be from a few minutes to several hours in each step, dependent upon the applied temperature. The reaction time is more than 10 minutes, preferably 30 minutes or more, 1 hour or more, 2 hours or more, 4 hours or more, 6 hours or more, or even longer if needed.

In a first aspect of the present invention, a C4-C6 monosaccharide in the form of an aldose or a mixture of such aldoses is/are isomerized over a suitable solid acidic zeolite catalyst, which catalyst comprises aluminum as the only metal forming part of the catalyst ("Zeolite-Al"), at a suitable elevated temperature for a suitable time in the presence of a suitable solvent to the corresponding 2-ketose or mixture of 2-ketoses.

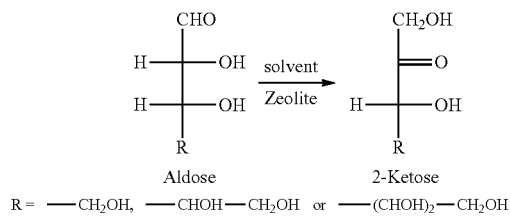

In the case of isomerization of C5 and C6 aldoses, a suitable alcohol is added in a first step of the reaction before an aqueous media may be added in a second step if desired. Addition of the aqueous media leads to hydrolysis of the ether product (R'-ketoside) of the first step and thus results in an even higher yield of the ketose.

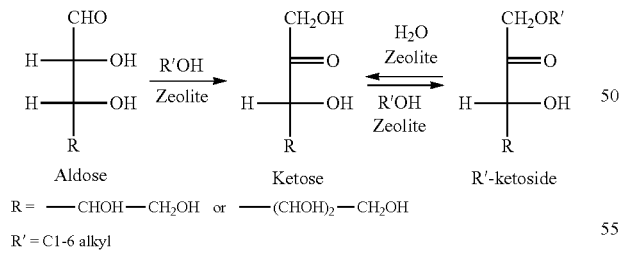

The aldose isomerized according to the present invention may be any aldose or mixture of aldoses selected from the group consisting of C4, C5 and C6 sugars containing an aldehyde group, which aldose group consists of the following natural sugars: erythrose, threose, ribose, arabinose, xylose, lyxose, allose, altrose, glucose, mannose, gulose, idose, galactose and talose (FIGS. 1-3). Both L and D sugars are included.

In accordance with the present isomerization reaction, the obtained C4-C6 ketoses belong to the ketose group comprising the natural sugars erythrulose, ribulose, xylulose, fructose, psicose, sorbose and tagatose (FIGS. 4-5), and may be obtained in yields similar to the yields reported for some of the sugars in enzymatic processes or by use of zeolite catalysts containing tin or other additional metal atoms as previously reported. The present invention however avoids use of sensitive biological material such as enzymes and use of tin and similar metals in the catalyst.

In a second aspect of the invention, the C4 aldoses erythrose and threose are isomerized over a suitable zeolite catalyst containing aluminum as the only metal ("Zeolite-Al") at a suitable elevated temperature in the presence of an aqueous media, e.g. water, to the corresponding 2-ketose, erythrulose.

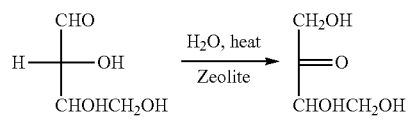

Erythrose and threose are isomerized in equilibrium to the erythrulose, in a reaction which can be shifted towards erythrulose by heating the aldose in an aqueous media, such as water, over a suitable zeolite catalyst (Scheme 1). Isomerizing erythrose and/or threose in a two-step reaction according to the present invention, i.e a first heating in the presence of an alcohol followed by heating in water leads to a low yield of erythrulose. A plausible reaction pathway is shown in Scheme 6, indicating that methyl erythroside presumably are not hydrolysed under the given conditions and thus accumulate in the reaction mixture. The C4 aldoses erythrose and threose are therefore preferably isomerized in a one-step reaction including only an aqueous media as solvent.

Scheme 1. Reaction pathway for the production of erythrulose via isomerization of erythrose and/or threose in water.

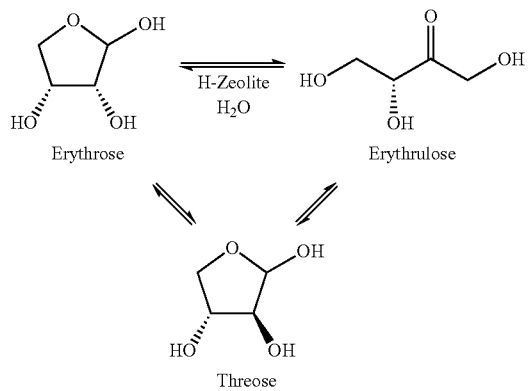

In a third aspect of the present invention, the C5 and C6 aldoses may be isomerized to the corresponding C5 and C6 ketoses in a one-step or a two-step reaction. In the one-step reaction (Schema 2 and Scheme 3, step 1), alcohol is used as solvent in the heating step in the presence of a suitable solid acidic zeolite catalyst (Zeolite-Al). In the reaction, the aldose is isomerized to the corresponding 2-ketose (part one of step 1), which in the presence of the alcohol is immediately converted into its alkyl ether form, the "alkyl ketoside", sometimes denoted "alkyl ketose" (part two of step 1).

Dependent upon the equilibrium between the ketose and the alkyl ketoside, accumulation of the ketoside may occur, which will lead to a limited yield of the desired ketone. Adding a hydrolysis step to the end of this one-step reaction will lead to less accumulation of the ketoside. Thus, the present invention also relates to a two-step reaction, comprising a first step in which the C5 and or C6 aldose(s) is/are heated in an alcohol over a suitable solid acidic zeolite catalyst (Zeolite-Al) to isomerize the aldose(s) to the corresponding 2-ketose(s), which in the presence of the alcohol is/are immediately converted into its/their alkyl ether form(s), the "alkyl ketoside(s)". Presence of an aqueous media such as water in step one, will lead to a low isomerization rate of C5 and C6 sugars and should therefore be avoided. At the end of reaction step one, the reaction mixture may be cooled prior to reaction step 2, for example to ambient temperature, or used without active cooling in reaction step 2. In a second step (Scheme 2 and Scheme 3, step 2), the alkyl ketoside(s) formed in step one is/are heated in the presence of an aqueous media and the zeolite catalyst in order to hydrate/hydrolyse the alkyl ketoside(s) (alkyl ether(s)) to the corresponding 2-ketose(s). In a preferred embodiment, the aqueous media is added to the reaction mixture of step without prior cooling. In another embodiment, the alcohol or part of it is removed after step 1 and before addition of the aqueous media. Preferably, water is added to the reaction mixture resulting from step 1 without removal of the alcohol. However, a certain excess of water is needed in order for the hydrolysis to take place. Both steps of the two-step reaction may conveniently be performed over the same zeolite in same reaction chamber in a so-called one-pot reaction. Two different reaction chambers may be applied for each of the two successive steps if desired.

In a first example, the C5 sugar xylose is isomerized to xylulose in a two-step one-pot process involving for example methanol and water as solvents in step 1 and step 2 respectively in the presence of a zeolite catalyst containing aluminum as the only metal. In the proposed pathway (Scheme 2), xylose is isomerized to xylulose, which in the presence of methanol is converted immediately by etherification to methyl-xyluloside. In the second step, addition of an aqueous media, such as water, drives the equilibrium between methyl-xylulose and xylulose towards xylulose in the presence of the catalyst. In both steps, heating is applied. The temperature and heating time is the same or different in the two steps, and is from about 60° C. to about 144° C., the melting point for xylose. Heating time is from about 30 minutes to about 6 hours dependent on the temperature. Preferably the temperature is 80° C. or more, 100° C. or more, 110° C. or more, or 120° C. or more. Preferably the heating/reaction time is 30 minutes or more, 60 minutes or more, 80 minutes or more, or 120 minutes or more. However, if the temperature is too high for too long, the xylose/xylulose may be converted into furfural or levulinic acid derivatives or similar undesirable downstream products.

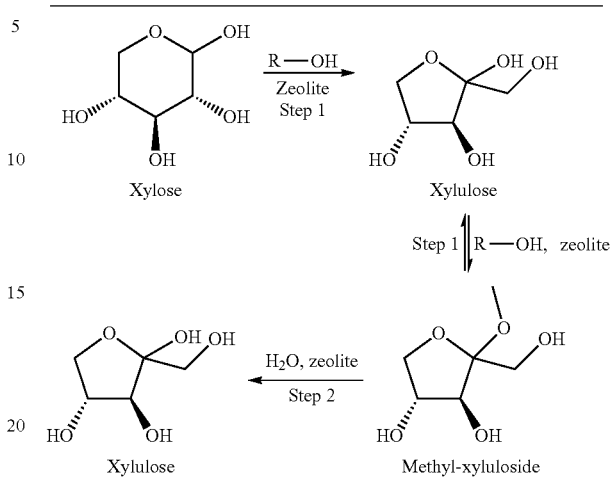

Scheme 2. Proposed reaction pathway for the production of xylulose via isomerization of xylose followed by the etherification of xylulose to methyl-xyluloside.

Lyxose can be converted to xylulose in the same way as described for xylose above. In a similar process, ribose and arabinose can be converted to ribulose. Additional isomerization, enzymatic or chemical, may be performed in order to obtain a preferred C5 ketose from any of the C5 aldoses. Both D and L forms of the C5 sugars may be converted according to the present invention.

In a second example, the C6 sugar glucose is converted to fructose in a two-step process involving for example methanol and water in step 1 and step 2 respectively, in the presence of a solid acidic zeolite catalyst containing aluminum as the only metal (Zeolite-Al). In the proposed pathway (Scheme 3), glucose is isomerized to fructose, which in the presence of methanol is immediately converted by etherification to methyl-fructoside (sometimes called methyl-fructose). In the second step, addition of an aqueous media, such as water, drives the equilibrium between methyl-fructose and fructose towards fructose in the presence of the catalyst. The reaction steps 1 and 2 may preferably be performed in a one-pot process. In both steps, heating is applied. The temperature and heating/reaction time is the same or different in the two steps, and is from about 60° C. to about 146° C., the melting point for D-glucose. Heating time is from about 30 minutes to about 6 hours dependent on the temperature. Preferably the temperature is 80° C. or more, 100° C. or more, 110° C. or more, and most preferred 120° C. or more. Preferably the heating/reaction time is 30 minutes or more, 60 minutes or more, 80 minutes or more, or 120 minutes or more. However, if the temperature is too high for too long, the glucose/fructose may be converted to levulinic acid and/or other undesirable downstream products.

Scheme 3. Proposed reaction pathway for the production of fructose via isomerization of glucose followed by the etherification of fructose to methyl-fructoside.

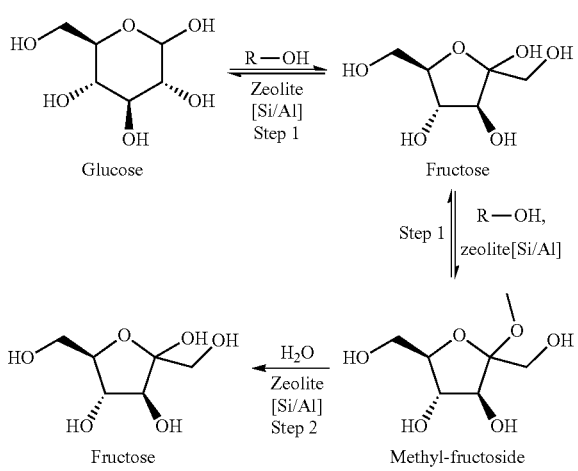

Mannose can be converted to fructose in the same way as described above (Scheme 4).

Scheme 4. Proposed reaction pathway for the production of fructose via isomerization of mannose followed by the etherification of fructose to methyl-fructoside.

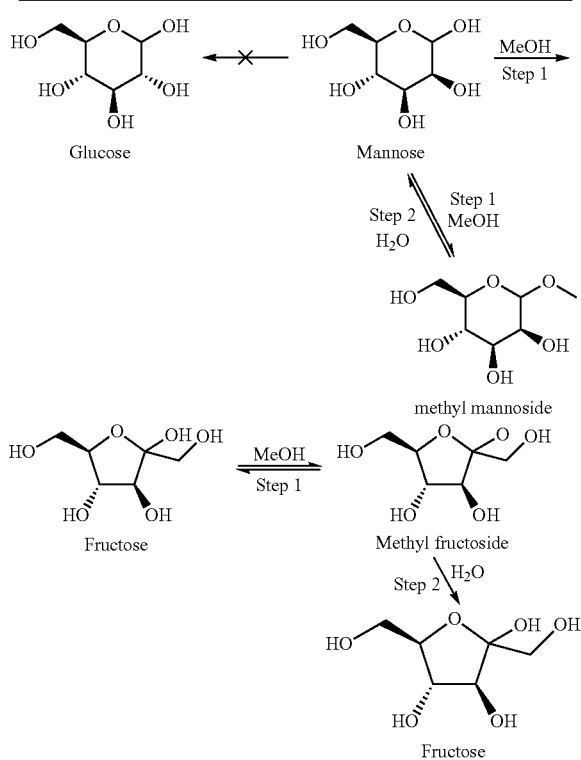

In a similar process, allose and altrose may be converted psicose, gulose and idose to sorbose and galactose and talose to tagatose. Additional isomerization, enzymatic or chemical, may be performed in order to obtain a preferred C6 ketose from any of the C6 aldoses. Both D and L forms of the C6 sugars may be converted according to the present invention.

In a further aspect of the invention, mixtures of different sugars in aldose forms can be converted by isomerization as discussed above. Such mixtures may be any artificial mixture(s) or mixtures obtained after chemical or enzymatic treatment of biological raw material such as disaccharides, e.g. sucrose, cellobiose, maltose, lactose, etc., oligosaccharides or polysaccharides such as inulin, starch, cellulose, hemicellulose and the like from biomass.

In another aspect of the invention the ketoses produced by the present invention are use as such, for examples as sweeteners in the food or brewery industry, or may be converted to a number of downstream molecules for use as platform chemicals in the chemical industry. Examples are lactic acid, 5-hydroxymethyl furfural, levulinic acid, etc.

In a yet another aspect of the invention, the use of a catalytic system as disclosed herein has the advantage of allowing the catalyst to be reused, as no loss of catalytic performance has been observed after at least five consecutive catalytic runs.

Studies of the effects of temperature, reaction time, solvent, sugar substrate and sugar concentration on the isomerization process of the present invention are disclosed below. By reference to the examples below, the optimal or preferred set of parameters for a desired conversion of aldoses or precursors thereof according to the present invention may easily be determined.

In accordance with the studies carried out as disclosed above and in the experimental section below, the present invention concerns a method of isomerizing C4-C6 aldose sugars to the corresponding 2-ketoses, comprising the step of providing a solution of a C4, C5 or C6 aldose sugar or a mixture of two or more such sugars in a suitable media, and heating said solution in the presence of a suitable solid acidic zeolite catalyst containing aluminum as the only metal ("Zeolite-Al") to a suitable temperature for a suitable time.

In one embodiment, the method comprises the steps of a) providing a solution of a C5 and/or C6 aldose sugar in a suitable alcohol, b) heating said solution in the presence of a suitable solid acidic zeolite catalyst containing aluminum as the only metal ("Zeolite-Al") to a suitable temperature for a suitable time, c) optionally adding an aqueous media to the alcoholic solution, and d) heating the aqueous solution in the presence of said zeolite catalyst to a suitable temperature for a suitable time. Preferably, the method is a one-pot method.

In another embodiment, the method according to the present invention concerns an isomerization, wherein the aldose is a C5 sugar and/or a C6 sugar, which method comprises the steps of a) providing a solution of said C6 and/or said C5 sugar(s) in a suitable alcohol, heating said solution in the presence of a suitable solid acidic zeolite catalyst, which catalyst contains aluminum as the only metal ("Zeolite-Al") to a temperature between 60 and 140° C. for between 20 minutes and 24 hours, adding an aqueous media, e.g. water, to the reacted mixture and heating the aqueous solution in the presence of said zeolite catalyst to a temperature between 60 and 130° C. for between 20 minutes and 24 hours.

In both heating steps, the temperature(s) may independently be 60, 80, 100, 120 or 130° C. or any temperature therein between for a suitable time. The temperature is adjusted to the aldose substrate. The higher the number of carbon atoms in the backbone, the higher the temperature may be applied. However, it should be noted, that the lower the temperature, the longer the heating/reaction time needs to be. For example if the temperature is chosen to be in the low end, e.g. 80° C., the heating time is preferable prolonged for up to about 24 hours. The reaction may include a cooling step, for example to ambient temperature, i.e. between 10 and 30° C., e.g. about 20° C., after the first heating/reaction, but before the addition of the aqueous media.

In a preferred embodiment, the C6 sugar is glucose and/or mannose and the corresponding ketose is fructose.

In another preferred embodiment, the C5 sugar is xylose and the corresponding ketose is xylulose.

The alcohol is selected from any C1-C6 alcohols, preferably a C1-C3 alcohol, such as methanol, ethanol, n-propanol or isopropanol. Most preferred is methanol.

In yet another embodiment, the method according to the present invention concerns an isomerization, wherein the aldose sugar is a C4 sugar or mixture of C4 sugars, which method comprises the steps of providing a solution of said C4 sugar(s) in a suitable aqueous media, e.g. water, heating said solution in the presence of a suitable solid acidic zeolite catalyst containing aluminum as the only metal ("Zeolite-Al") to a temperature between 60 and 130° C. for between 20 minutes and 24 hours.

In a further embodiment the C4 sugar is erythrose and/or threose and the corresponding ketose is erythrulose.

A suitable zeolite catalyst for use in the present invention is a solid acidic zeolite with large pores, i.e. a pore size above 5 Å, preferably between 6 and 12 Å and a suitable Si/Al ratio, and the zeolite catalysts is substantially free of any tetravalent metal atoms, such as tin (Sn), titanium (Ti), zirconium (Zr), hafnium (Hf) and germanium (Ge). Preferably, the solid zeolite catalyst is selected from HY or Hbeta catalysts with a suitable Si/Al ratio.

The reaction time in the two heating steps are independently between 20 minutes and 24 hours, more preferably between 20 minutes and 10, 8, 6, 4, 2 or 1 hours, or between 30 minutes and 6, 4, 2 or 1 hours, or between 1 hour and 2, 4 or 6 hours.

The aldose sugar(s) may be obtained from any precursor thereof, e.g. from naturally occurring biological raw material, e.g. biomass, such as bio-waste, for example disaccharide(s), e.g. sucrose, cellobiose, lactose or maltose, oligosaccharides or polysaccharides, e.g. inulin, starch, cellulose and/or hemicellulose or the like in an enzymatic and/or chemical process.

Further, the ketoses obtained according to the present invention may be used as sweeteners in the food or brewery industry, or treated enzymatically or chemically in order to obtain downstream platform chemicals such as lactic acid, HMF, levulinic acid, furfural, etc.

EXAMPLES

Selection and Optimization of Catalyst, Solvents, Time and Concentration

Example 1 (C6-sugars, Illustrated by Isomerization of Glucose and Mannose to Fructose)

Chemicals

Glucose (99.5%), fructose (99%), mannose (99%), methanol (99.9%), ethanol (99.9%) and propanol (99.7%) were purchased from Sigma-Aldrich. All the commercially available zeolites used throughout this study were kindly provided by Zeolyst International. The zeolites are pure and do not contain any binder material. The zeolites received in the $NH_4$-form were calcined at 550° C. in static air for 6 h prior to use in order to produce the acidic form (H-form).

Reaction Procedure

The reaction was carried out in methanol following a two-step batch mode of operation. The proposed reaction pathway for the conversion of glucose to fructose is shown in Scheme 3. In the first step, glucose is isomerized to fructose that reacts immediately with the methanol present in the reaction media as a solvent to form methyl fructoside. In order to obtain fructose, water is added in a second step to hydrolyze the methyl fructoside formed during the first step.

Catalytic batch experiments were performed in Ace pressure tubes. In the first reaction step, typically 75 mg of catalyst, 125 mg of sugar, and 4 g of alcohol or water were added and mixed in the tube using a magnetic stirrer. The tube was then heated to a desired reaction temperature by positioning it in a thermally controlled oil bath preset at a desired reaction temperature in the range 60-120° C. After a certain reaction time, the tube was removed from the oil bath and cooled down to room-temperature quickly. In the second reaction step, 4 g of water was added to the resulting reaction mixture, where after the tube was placed into an oil bath at 120° C. during 1 h.

Analysis of the Reaction Products

Reaction samples were analyzed by liquid chromatography. Glucose was determined in a HPLC Agilent 1200 Series with a Aminex HPX-87H column (Bio-Rad), using 0.005 M aqueous sulfuric acid as eluent at a flow rate of 0.6 ml/min, and a column temperature of 60° C. Fructose, mannose and methyl fructoside were analyzed in a HPLC Agilent 1200 Series with a Rezex RCM-Monosaccharide $Ca^{2+}$ column (Phenomenex), using MiliQ water as mobile phase at a rate of 0.6 ml/min and a column temperature of 80° C. Both HPLC instruments are equipped with a refractive index detector. It was not possible to obtain a standard of methyl fructoside so the identification was made by $^{13}C$ NMR and the response factor was obtained through several reactions from fructose at low temperature assuming no formation of others by-products. Fructose, mannose and their corresponding alkyl-derivatives merge at the same retention time using the Aminex column, what can easily lead to an error in the quantification. On the other hand, glucose and methyl fructoside elute at very similar retention times with Monosaccharide column. For determination, the symmetry of the peak was used and the ether was quantified using the right half of the peak. After the second step, the amount of this compound was so little that the quantification was impossible by HPLC. Catalytic results are shown in terms of product distribution reported as mol % (molar amount of each product present in the reaction mixture divided by the total molar amount of starting sugar). No humins were observed in any of the C6 sugar isomerization in methanol experiments either during the first step or the second step. In some cases, a major unidentified peak (retention time=12.9) has been observed in HPLC chromatogram between glucose (retention time=11.3) and fructose (retention time=14.0) and a minor peak has also appeared just before fructose. "Others" are unidentified products and calculated for glucose as the starting substrate: 100-(glucose+fructose+methyl-fructoside), for mannose as staring substrate: 100-(mannose+fructose+methyl-fructoside) and for fructose as staring substrate: 100-(fructose+methyl-fructoside). Similar calculations were made for the C5 sugar isomerization.

Results

Catalysts

In a first preliminary test, basic zeolite catalysts (Na-Y and Na-Mor) were tested for their ability to isomerize glucose to fructose. Some of the basic catalysts isomerized glucose slightly, but as they are not able to catalyze the etherification of fructose to methyl-fructoside, the highest amount of fructose produced was around 18% (Table 1). Also, acidic form zeolites (H-ZSM-S and H-MOR) were been tried, but only low glucose conversion is achieved in the isomerization reaction.

TABLE 1

Product distribution obtained from glucose conversion over commercial zeolite catalysts. Step 1: 75 mg catalyst, 125 mg of glucose, 4 g methanol, 1 h, 120° C.; Step 2: 4 g water, 1 h, 120° C.

| Form | Zeolite | Pore dimensions (Å) | Si/Al | Step | Glucose | Fructose | Others | MF |
|---|---|---|---|---|---|---|---|---|
| Basic form | NaY | 7.4-11.8 | 2.6 | 1 | 87.6 | 12.4 | 0 | — |
| | NaMOR | 6.5 × 7.0 2.6 × 5.7 | 10 | 1 | 80.6 | 18.1 | 1.3 | — |
| Acidic form | HZSM5 | 5.3 × 5.6 5.1 × 5.1 | 11.5 | 1 | 83 | 8 | 7.1 | — |
| | | | 25 | 1 | 77.2 | 11 | 10.4 | — |
| | | | 40 | 1 | 90.2 | 5.9 | 1.1 | — |
| | | | 140 | 1 | 95 | 3.8 | 2.6 | — |
| | HMOR | 6.5 × 7.0 2.6 × 5.7 | 10 | 1 | 92.8 | 3.7 | 2.6 | — |
| | HY | 7.4-11.8 | 2.6 | 1 | 56.1 | 16.3 | 8.4 | 19.2 |
| | H-USY | | | 2 | 53.8 | 19.8 | 8.8 | 17.6 |
| | | | 6 | 1 | 30.0 | 22.4 | 15.1 | 32.5 |
| | | | | 2 | 27.9 | 54.8 | 13.6 | 3.7 |
| | | | 30 | 1 | 63.3 | 25.5 | 11.1 | — |
| | | | | 2 | 63.2 | 24.2 | 12.6 | — |
| | HBeta | 6.4 × 7.6 5.5 × 5.5 | 12.5 | 1 | 29.3 | 23.3 | 25.3 | 22.1 |
| | | | | 2 | 30.2 | 40.2 | 21.6 | 8.0 |
| | | | 19 | 1 | 39.3 | 21.1 | 23.6 | 16.0 |
| | | | | 2 | 42.8 | 28.9 | 20.2 | 8.0 |
| | | | 150 | 1 | 90.4 | 0.0 | 9.6 | — |
| | | | | 2 | 88.7 | 0.0 | 11.3 | — |

In another preliminary test, different commercially available acidic zeolite catalysts were tested in the isomerization of glucose to fructose including isomerization and etherification of glucose to methyl-fructoside at 120° C. and 1 hour of reaction, followed by addition of water and an extra hour of heating in order to obtain the fructose from the methyl-fructoside. As can be observed from Table 1, the best results were achieved using the large pore zeolites, BEA (H-Beta) and Y. Using the H-USY-6 and H-Beta-12.5, 55 and 40% of fructose were obtained, respectively.

The most active zeolite was Y, more active than beta, ZSM-5 and mordenite zeolites. After 1 h at 120° C., the yields of fructose using H-USY (Si/Al=6) was 55%. Pore size limitations, substrate sizes, and catalyst surface area all contribute to the strong activity of H-USY-6 for glucose and xylose isomerization. The zeolite H-USY-6 is a commercially available and a cheap catalyst without incorporated toxic metals which is ease to reuse. An advantage of doing the reaction in alcohol is that wastewater is minimized and products can be purified by distillation.

In addition to pore size, pore structure is also an important point. Thus, the large cages present in the Y-zeolite framework allow the highest yields of methyl-fructoside in the first step which is converted back into fructose during the second step.

From Table 2, it can be understood by analyzing $NH_3$-TPD (Temperature Programmed Desorption) results that H-USY-6 with a ratio of acid sites type 1: type 2 of 1:0.81 and for H-Beta-12.5 an acid sites type ratio of 1:0.52 gave the highest yield of fructose (Table 2). It can be apparently understood that zeolites contain both medium (approximately between 100 and 270° C.) and strong acid sites (approximately between 270 and 500° C.). The ratio of the number of medium acidic sites (type 1) to strong acidic sites (type 2) can be taken as a measure defining the relative efficiency of the catalysts for the formation of fructose from glucose. Above or below the mentioned acid site ratios or with zeolites having a lower number of total acid sites, a lower yield of fructose is obtained. The ratio of Lewis and Brnsted acidity is thus a key factor to maximize the glucose conversion.

TABLE 2

Acidity measurements from $NH_3$-TPD.

| Catalyst | Pore size | Si/Al ratio | Acid sites type 1 (100-270° C.) (μmol/g) | Acid sites type 2 (270-500° C.) (μmol/g) | Total acid sites (μmol/g) | Acid sites type 1/type 2 ratio | Fructose (%) |
|---|---|---|---|---|---|---|---|
| H-Y | Large pore | 2.6 | 699 | 252 | 951 | 1:0.36 | 20 |
| H-USY | | 6 | 461 | 374 | 835 | 1:0.81 | 55 |
| | | 30 | 182 | 165 | 347 | 1:0.91 | 24 |
| H-Beta | | 12.5 | 563 | 292 | 855 | 1:0.52 | 40 |
| | | 19 | 440 | 366 | 806 | 1:0.83 | 29 |
| | | 150 | 71 | 76 | 147 | 1:1.07 | 0 |
| H-ZSM-5 | Medium pore | 40 | 211 | 240 | 451 | 1:1.14 | 6 |

TABLE 3

Product distribution obtained from fructose and mannose conversion over commercial zeolite catalyst. Step 1: 125 mg fructose or mannose, 4 g methanol, 1 h, 120° C.; Step 2: 4 g water, 1 h, 120° C.

| Substrate | Zeolite | Si/Al | Step | Glucose | Mannose | Fructose | Others | MF |
|---|---|---|---|---|---|---|---|---|
| Fructose | H-USY | 6 | 1 | 0.0 | 0.0 | 18.3 | 0 | 81.7 |
| | | | 2 | 0.0 | 0.0 | 73.5 | 0 | 26.5 |
| | | 30 | 1 | 0.0 | 0.0 | 19.1 | 0 | 80.9 |
| | | | 2 | 0.0 | 0.0 | 77.7 | 0 | 22.3 |
| | H-Beta | 12.5 | 1 | 0.0 | 0.0 | 22.6 | 0 | 77.4 |
| | | | 2 | 0.0 | 0.0 | 79.4 | 0 | 20.6 |
| Mannose | H-USY | 6 | 1 | 0.0 | 3.5 | 19.4 | 47.4 | 29.7 |
| | | | 2 | 0.0 | 7.4 | 56.3 | 30.1 | 6.3 |
| | | 30 | 1 | 0.0 | 5.3 | 26.4 | 63.9 | 4.4 |
| | | | 2 | 0.0 | 25.0 | 32.1 | 42.0 | 0.9 |
| | H-Beta | 12.5 | 1 | 0.0 | 4.5 | 12.6 | 70.4 | 12.5 |
| | | | 2 | 0.0 | 20.3 | 26.9 | 50.2 | 2.7 |

To understand the equilibrium between glucose-fructose-mannose, the study was further extended. Experiments were carried out with H-USY and HBeta zeolites and fructose and mannose as starting sugars. The results are summarized in Table 3. The results apparently indicate that there was no glucose formation neither from fructose nor from mannose irrespective of which catalysts was used, implying that these three sugars are not in equilibrium. The results from fructose suggested further, that it can only form methylfructoside which is converted back into fructose. In the case of mannose, H-USY-6 yielded 56% of fructose after the second step and it can also be seen that mannose reappeared and increased from 4 to 7%. A similar effect can apparently be seen for HBeta 12.5, which induced reappearance of mannose from 5 to 20% after the second step. Some of the unidentified other sugars products can be methylated mannose, that can be hydrolysed back to mannose after the addition of water (Scheme 5).

Solvent, Temperature and Time

To understand the role of methanol and water for the glucose isomerisation, experiments were carried out to examine the synthesis of fructose from glucose in methanol using different solvent mixtures from 1 to 95 wt. % of methanol in water (Table 4). Here, no significant formation of fructose from glucose was observed (8% of maximum yield of fructose observed) and the formation of methylfructoside (MF) was not detected, thus implying that glucose isomerization needs to be carried out first in methanol and subsequently in water. Previously, it has been reported that in order to maximize the conversion of fructose into methylfructoside, it was necessary to use a large excess of alcohol, as well as removing the water formed during the reaction. Since the presence of water at the beginning of the reaction is unfavorable, it was decided that the reaction should following a two-steps mode, at least for C5 and C6 sugars.

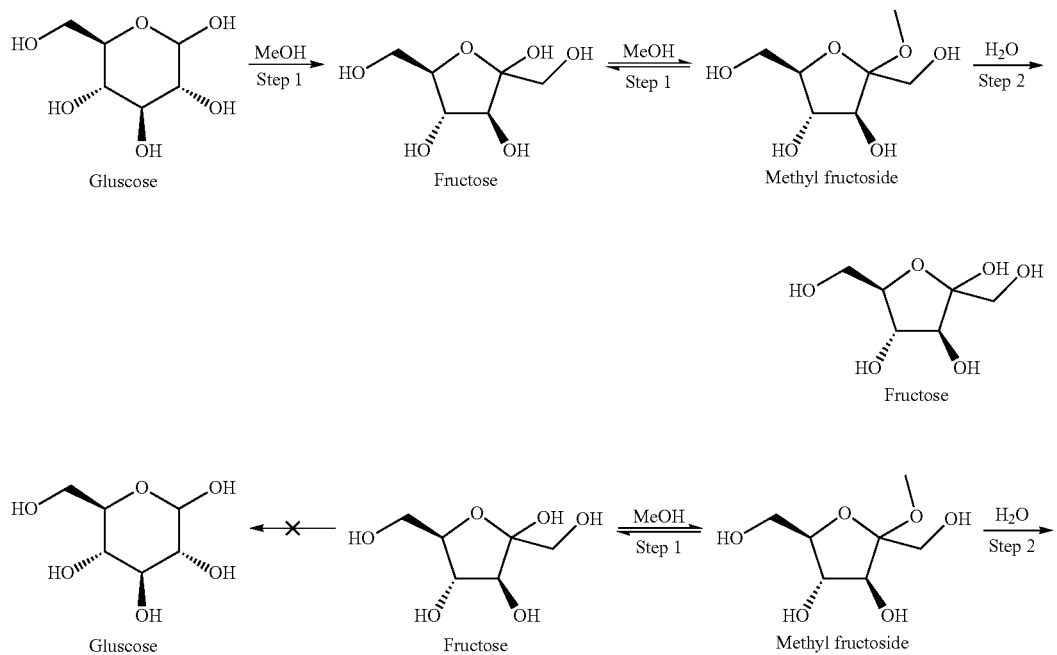

Scheme 5. The plausible pathway for the formation of fructose from glucose, mannose and fructose.

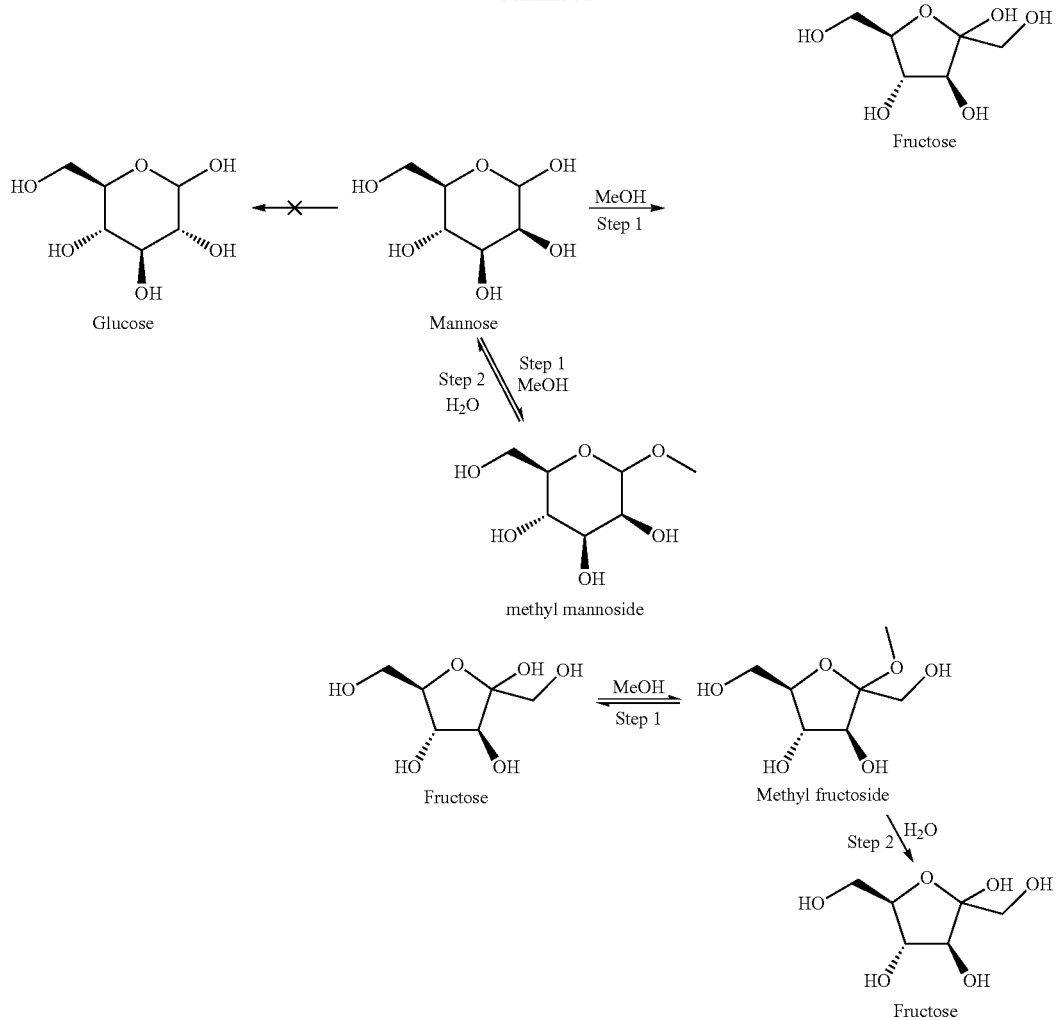

The optimal amount of water and time to be selected in step 2 were chosen after some preliminary studies shown in the FIG. 6. The reaction conditions were: step 1: 75 mg H-USY-6, 125 mg glucose, 1 h, 120° C., 4 g methanol; step 2: 1, 2 or 4 hour with 0.5, 2 or 4 g water at 120° C.

TABLE 4

"One-pot" synthesis of fructose from glucose in methanol. Reaction conditions: 75 mg H-USY-6, 125 mg glucose, 4 g solvent mixture, 1 h, 120° C.

| MeOH/Water (%) | Products distribution (mol %) | | |
|---|---|---|---|
| | Glucose | Fructose | MF |
| 1 | 100 | 0 | 0 |
| 20 | 100 | 0 | 0 |
| 40 | 100 | 0 | 0 |
| 60 | 100 | 0 | 0 |
| 80 | 95 | 3 | 0 |
| 95 | 86 | 8 | 0 |
| 99 | 33 | 22 | 29 |

The influence of reaction temperature has also been studied and results are given in Table 5. As the reaction temperature increased, the formation of methyl-fructoside in the first step and the formation of fructose in the second step increased. At 60° C., the yield of fructose was 3% and it is retained even after the second step in water. Already at 80° C., a significant amount of fructose was observed, but the highest yield was seen at 120° C.

TABLE 5

Effect of the temperature for glucose conversion. Step 1: 75 mg catalyst, 125 mg glucose, 4 g methanol, 1 h; Step 2: 4 g water, 1 h, 120° C.

| T (° C.) | Step | Glucose | Fructose | Others | MF |
|---|---|---|---|---|---|
| 60 | Step 1 | 97.5 | 2.5 | 0.0 | 0.0 |
| | Step 2 | 97.3 | 2.7 | 0.0 | 0.0 |
| 80 | Step 1 | 89.1 | 10.9 | 0.0 | 0.0 |
| | Step 2 | 88.3 | 11.7 | 0.0 | 0.0 |
| 100 | Step 1 | 64.9 | 11.7 | 8.6 | 14.8 |
| | Step 2 | 64.4 | 28.4 | 8.0 | 0.0 |
| 120 | Step 1 | 30.0 | 22.4 | 15.1 | 32.5 |
| | Step 2 | 27.9 | 54.8 | 13.5 | 3.7 |

To measure the rate of formation of methyl-fructoside in methanol, time-course study was carried out for each sugar at 80° C. and the results are shown in FIG. 7. After 1 h, a very small amount of methyl-fructoside was observed. As the time increased, the formation of methyl-fructoside increased to a yield of 35% after 24 h. In the case of mannose, similar results were obtained and the yield of methyl-fructoside and fructose were 35 and 16%, respectively. The results demonstrate that longer reaction time is needed to increase the yield of methyl-fructoside if the reaction is carried out at low temperatures. FIG. 7 also shows that aldoses glucose and mannose are isomerized and the amount of fructose and methyl-fructoside are built up over time in step 1, and that an equilibrium is established between fructose and methyl-fructoside. Furthermore, only fructose and methyl-fructoside were formed when using mannose as starting sugar. With these results, there is no evidence of equilibrium between glucose, mannose and fructose in methanol. The use of methanol as a solvent in the isomerization of glucose to fructose is a way to break the equilibrium of the C6 isomers described in water.

Changing the solvent from methanol to higher alcohols leads to the formation of the corresponding alkyl-fructoside (FIG. 8). The same pathway described for methanol is observed, with an increase of the amount of fructose after adding water in the second step. However, the fructose etherification with larger alcohols seems to be more difficult, probably due to steric impediments. Therefore, less fructose and more byproducts are detected in comparison with methanol. No fructose production is observed in aqueous solvent that confirming the crucial role of alcohol for the isomerization of glucose.

Concentration of the Substrate

Another important aspect to take into account is the possibility of increase the initial glucose concentration in the isomerization reactions. Therefore, some experiments with different initial concentration of glucose over H-USY-6 were carried out. FIG. 9 shows a progressive decrease in the yield of fructose from 55% at 3 wt. % of initial glucose concentration to 27% at 16.7 wt. %, probably due to the higher presence of water formed during the etherification step. However, acceptable results are obtained up to 9.1 wt % of initial glucose, with a fructose yield of 38%. That value increased to 46% at longer reaction time, getting yields similar to that obtained with lower initial glucose concentration.

The influence of catalyst loading with different glucose-to-catalyst mass ratios between 1.7:1 and 12.6:1 was examined in a reaction system with H-USY-6 and a 3 wt % initial glucose concentration in methanol. The reaction time was optimized during each reaction step to achieve high yields of fructose. The results (Table 6) clearly demonstrate that it is possible to achieve above 50% of fructose for all the systems examined if the reaction times were adjusted properly.

TABLE 6

The influence of glucose to H-USY-6 catalyst mass ratio on the product distribution in the two-step reaction sequence. Step 1: 10-75 mg catalyst, 125 mg glucose, 4 g methanol, 120 °C.; Step 2: 4 g water, 120 °C.

| | $m_{glu}:m_{cat}$ | | | Product distribution (%) | |
|---|---|---|---|---|---|
| $m_{cat}$ (mg) | ratio | Step | Time (h) | Glucose | Fructose |
| 10 | 12.5:1 | 1 | 21 | 39 | 20 |
| | | 2 | 3 | 37 | 51 |
| 15 | 8.3:1 | 1 | 5 | 40 | 18 |
| | | 2 | 3 | 38 | 52 |
| 25 | 5.0:1 | 1 | 4 | 32 | 19 |
| | | 2 | 3 | 33 | 53 |
| 50 | 2.5:1 | 1 | 3 | 32 | 20 |
| | | 2 | 1 | 33 | 55 |

TABLE 6-continued

The influence of glucose to H-USY-6 catalyst mass ratio on the product distribution in the two-step reaction sequence. Step 1: 10-75 mg catalyst, 125 mg glucose, 4 g methanol, 120 °C.; Step 2: 4 g water, 120 °C.

| | $m_{glu}:m_{cat}$ | | | Product distribution (%) | |
|---|---|---|---|---|---|
| $m_{cat}$ (mg) | ratio | Step | Time (h) | Glucose | Fructose |
| 75 | 1.7:1 | 1 | 1 | 30 | 22 |
| | | 2 | 1 | 28 | 55 |

Reuse of Catalyst

Catalyst life has also been evaluated for the most active catalyst selected in the screening of catalysts, H-USY-6. FIG. 10 depicts the results of five consecutive catalytic runs performed reusing the catalyst under the optimal reaction conditions. After each catalytic run, recovering of the catalyst was performed by filtration, washed through with methanol and dried overnight at 140° C. before being used again in a new reaction. It can be seen a constant fructose yield around 40-50% in all the catalytic runs. From the results shown in FIG. 10, no loss of catalytic performance is observed keeping a similar product distribution after five consecutive catalytic runs.

Example 2 (C5-Sugars)

Isomerization of Xylose

The isomerization of the C5 sugar xylose to xylulose is an important transformation in carbohydrate chemistry, among other reasons, because xylulose is an intermediate compound to make, e.g. furfural by dehydration. Accordingly, the following experiments were carried out with xylose as starting sugar over solid zeolite catalysts.

Chemicals

Xylose (99.5%), xylulose (99%), methanol (99.9%), ethanol (99.9%) and propanol (99.7%) were purchased from Sigma-Aldrich. D-xylose (1.0 M aqueous solution) was purchased from Omicron Biochemicals. All the commercially available zeolites used throughout this study were kindly provided by Zeolyst International. The zeolites were treated prior to use in order to produce the acidic form (H-form) as described in Example 1.

Reaction Procedure

The reaction was carried out in methanol following a two-step batch mode of operation, unless otherwise described. The proposed reaction pathway for the conversion of xylose to xylulose is shown in Scheme 2. In the first step, xylose is isomerized to xylulose that reacts immediately with the methanol present in the reaction media as a solvent. In order to obtain xylulose, water is added in a second step to hydrolyze the methyl-xyluloside formed during the first step.

Catalytic batch experiments were performed in Ace pressure tubes and analyzed as described in Example 1.

Catalysts

In a preliminary test, some basic zeolite catalysts (Na-Y and Na-Mor) and some acidic form zeolites (H-ZSM-5, H-MOR, H-Y and H-Beta) were tested for their ability to isomerize xylose to xylulose.

The different commercially available acidic zeolite catalysts were tested in the isomerization of xylose (and lyxose) to xylulose. As can be observed from Table 7, the best results were achieved using the large pore zeolites, beta and Y. Using the H-USY-6 and H-Beta-12.5, 50 and 39% of xylulose were obtained, respectively. As for the C6 sugars, the most active zeolite was H-USY, more active than H-Beta, H-ZSM-5 and mordenite zeolites.

The product distribution resulting from isomerization of xylose over different acidic zeolites was determined in a 2-step test after step 1 and after step 2. From Table 7, it can be seen that step 2 results in a higher yield of xylulose.

TABLE 7

Products distribution obtained for xylose conversion over commercial catalysts after the first and second step. Step 1: 75 mg catalyst, 125 mg xylose, 4 g methanol, 1 h, 100° C.; Step 2: 4 g water, 1 h, 100° C.

| zeolite | Si/Al | Reaction step | Xylose | Xylulose | Others |
|---|---|---|---|---|---|
| Na-Y | 2.6 | 1 | 97.5 | 2.5 | 0 |
| Na-MOR | 10.0 | 1 | 97 | 3 | 0 |
| H-ZSM-5 | 11.5 | 1 | >98 | <0.5 | 0 |
|  | 25 | 1 | >98 | 1 | 0 |
|  | 40 | 1 | >98 | <0.5 | 0 |
|  | 140 | 1 | >98 | <0.5 | 0 |
| H-MOR | 10 | 1 | 97 | 2 | 0 |
| H-Y | 2.6 | 1 | 66 | 23 |  |
|  |  | 2 | 64.8 | 25.0 | 10.2 |
| H-USY | 6 | 1 | 32 | 44 |  |
|  |  | 2 | 31.6 | 50.5 | 18.0 |
|  | 30 | 1 | 92 | 4 |  |
|  |  | 2 | 87.3 | 4.4 | 8.3 |
| H-Beta | 12.5 | 1 | 46 | 31 |  |
|  |  | 2 | 44.5 | 38.9 | 16.6 |
|  | 19 | 1 | 71 | 16 |  |
|  |  | 2 | 70.8 | 19.8 | 9.4 |
|  | 150 |  | 100 | 0 | 0 |
| H-Y* | 6 | 1 | 21 | 31 |  |
|  |  | 2 | 19 | 36 | 45 |

*Lyxose was used as substrate

Solvent, Temperature and Time

The amount of water to be selected in step 2 was chosen after some preliminary studies shown in the FIG. 11. A small increase in yield was seen with the high amount of water. The reaction conditions were: step 1: 75 mg H-USY-6, 125 mg xylose, 4 g methanol, 1 h, 100° C.; step 2: 1 hour with 0.5, 2 or 4 g water at 100° C.

The effect of temperature and time for isomerization of xylose to xylulose was tested and the results are presented in Table 8. It can be seen from the table that xylose can isomerise to xylulose in similar yield as observed for the glucose isomerisation reaction.

Changing the solvent from methanol to higher alcohols leads to the formation of the corresponding alkyl xylulose (FIG. 12). The same pathway described for methanol is observed, with an increase of the amount of xylulose after adding water in the second step. However, the xylulose etherification with larger alcohols seems to be more difficult. No xylulose production is observed in aqueous solvent that confirming the crucial role of alcohol for the isomerization of xylose.

TABLE 8

Effect of the temperature for xylose conversion.
Step 1: 75 mg catalyst, 125 mg xylose, 4 g methanol, 24 h; Step 2: 4 g water, 1 h, 120° C.

| T (° C.) | Time (h) | Solvent | Step | xylose | xylulose | Others |
|---|---|---|---|---|---|---|
| 60 | 24 | MeOH | Step 1 | 24 | 32 | 44 |
| 120 | 1 | Water | Step 2 | 21 | 40 | 39 |
| 80 | 24 | MeOH | Step 1 | 15 | 33 | 52 |
| 120 | 1 | Water | Step 2 | 11 | 35 | 54 |

Concentration of the Substrate

Experiments with different initial concentration of xylose over H-USY-6 were carried out in order to find the optimal concentration of the substrate. FIG. 13 shows a progressive decrease in the yield of xylulose from 50% at 3 wt. % of initial xylose concentration to 25% at 16.7 wt % Acceptable results are obtained up to 9.1 wt % of initial xylose, with a xylulose yield of 36%.

Reuse of Catalyst

Catalyst life was evaluated for the most active catalyst selected in the screening of catalysts, H-USY-6 in the same way as for C6-sugars as substrate. From FIG. 14 it can be seen that no loss of catalytic performance is observed keeping a similar product distribution after five consecutive catalytic runs.

Example 3 (C4-Sugars)

Isomerization of Erythrose

Chemicals

Aqueous solution of erythrose (0.093M), erythrulose (0.522M), Threose (0.47 M), were purchased from Omicron Biochemicals. Erythrose (>75%) erythrulose (>85%), methanol (99.9%) were purchased from Sigma-Aldrich. All the commercially available zeolites used throughout this study were kindly provided by Zeolyst International. The zeolites were treated prior to use in order to produce the acidic form (H-form) as described in Example 1.

Reaction Procedure

The reaction was carried out in water in a one-step batch mode or in methanol following a two-step batch mode of operation. A plausible reaction pathway for the isomerisation of C4-sugars in methanol is shown in Scheme 6.

Scheme 6. Catalytic batch experiments were performed in Ace pressure tubes and analyzed as describes in Example 1.

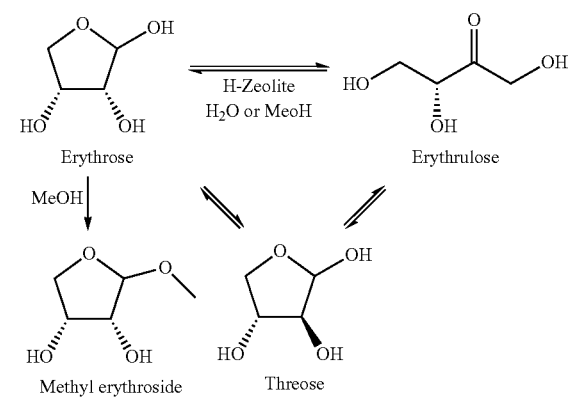

Catalysts

The different commercially available acidic zeolite catalysts were tested in the isomerization of erythrose and threose to erythrulose. As can be observed from Table 9, the best results were achieved using the large pore zeolites, H-Beta and H-Y after 5 hours. Using the H-USY-6 and H-Beta-12.5, 44 and 26% of erythrulose were obtained, respectively.

TABLE 9

Isomerisation of Erythrose in aqueous medium over zeolites.
Reaction conditions: Erythrose = 0.0632 g of 0.093M;
Catalyst (H-USY-6) weight = 0.0375 g; Water =
5.58 g; Temp. = 120° C. *The reaction temperature
was 100° C.

| | Product distribution (%) | | | | | | | | |
|---|---|---|---|---|---|---|---|---|---|
| | Erythrose | | | Erythrulose | | | Threose | | |
| Catalysts | 1 h | 3 h | 5 h | 1 h | 3 h | 5 h | 1 h | 3 h | 5 h |
| H-Y-2.6 | 65 | 30 | 16 | 26 | 37 | 36 | 1 | 3 | 5 |
| H-USY-6 | 74 | 48 | 32 | 23 | 39 | 45 | <1 | 1.5 | 4 |
| H-USY-30 | 97 | 90 | 84 | 2 | 4 | 6 | <0.1 | <0.1 | <0.1 |
| H-Beta-2.5 | 88 | 71 | 38 | 8 | 19 | 26 | <0.1 | 1 | 1.3 |
| H-Beta-19 | 95 | 86 | 78 | 2 | 4 | 6 | <0.1 | <0.1 | <0.1 |
| H-USY-6* | 92 | | | 7 | | | <0.2 | | |

Erythrose and to a lesser extent threose are converted into erythrulose in a progressive increase with time as shown in Table 9 and FIG. 15. Table 10 shows that erythrose disappears, but is only converted into erythrulose in smaller amount in the presence of methanol. It is likely that erythrose is converted to methyl-erythroside in methanol, however without hydrolysis in step 2.

TABLE 10

Isomerisation of tetroses in water and methanol. Reaction
conditions: C4 sugar = 0.0632 g of 0.093M; H-USY-6 =
0.0375 g; Water = 5.58 g; Temp. = 120° C. *1.04 mmol
of erythrose (>75%) was dissolved in methanol (4, g) and
the reaction was carried out in presence of H-USY-6 (75 mg)
at 80° C. for 1 h. After 1 h, the methanol was removed
and 5 g of water added to the reaction mixture and analyzed
in HPLC.

| | Product distribution (%) | | | | | | | | |
|---|---|---|---|---|---|---|---|---|---|
| | Erythrose | | | Erythrulose | | | Threose | | |
| Substrate | 1 h | 3 h | 5 h | 1 h | 3 h | 5 h | 1 h | 3 h | 5 h |
| Erythrose | 74 | 60 | 32 | 22 | 31 | 44 | <1 | 1.5 | 4 |
| Erythrulose | 2 | 4 | 5 | 95 | 81 | 62 | 2 | 5 | 7 |
| Threose | <0.5 | 1 | 2 | 13 | 26 | 32 | 85 | 68 | 56 |
| Erythrose* | 4 | | | 18 | | | 5 | | |

TABLE 11

Reaction Conditions: Erythrose = 0.0632 g of 0.093M; Catalyst =
H-USY-6; Water = 5.58 g; Temp. = 120° C.; Time = 3 h.

| $m_{cat}$ (mg) | $m_{eryth}$:$m_{cat}$ ratio | Time (h) | Product distribution (%) | | | Total sugar (%) |
|---|---|---|---|---|---|---|
| | | | Erythrose | Erythrulose | Threose | |
| 5 | 12.6:1 | 3 | 81 | 13 | <0.5 | 94 |
| | | 7 | 56 | 34 | 2 | 91 |
| 10 | 6.3:1 | 3 | 70 | 21 | 1 | 92 |
| | | 5 | 58 | 33 | 1 | 93 |
| | | 7 | 49 | 40 | 2 | 91 |
| 15 | 4.2:1 | 3 | 70 | 23 | 1 | 94 |
| | | 5 | 58 | 36 | 2 | 95 |
| | | 7 | 42 | 45 | 3 | 88 |
| 37.5 | 1.7:1 | 3 | 57 | 34 | 1 | 92 |
| | | 5 | 32 | 45 | 4 | 81 |

The influence of catalyst loading with different erythrose-to-catalyst mass ratios between 1.7:1 and 12.6:1 was examined in a reaction system with H-USY-6 and an initial erythrose concentration of 0.0632 g of 0.093M in 5.58 g water. The reaction time was optimized during each reaction step to achieve high yields of erythrulose. The results (Table 11) clearly demonstrate that it is possible to optimize the yield by adjusting the reaction time to the catalyst loading.

Example 5

Temperature Programmed Desorption Studies (NH$_3$-TPD)

The number of acid sites present in the zeolites was measured by using an AutoChem II 2920 apparatus from Micromeritics. 100 mg of the sample was placed in a quartz reactor and degassed at 500° C. for 1 h in a flow of helium at the rate of 50 ml/min. The reactor was then cooled to 100° C. and ammonia (50 ml/min) was allowed to get adsorbed at the same temperature for 2 h. Before the ammonia desorption measurement, the sample was flushed with helium at the rate of 50 ml/min to remove the physisorbed ammonia. Ammonia desorption was measured every one second from 100 to 500° C. at a ramp of 10° C./min. The number of acid sites is calculated as the area under the curve. The results are shown in Table 2. It can be apparently understood that zeolites contain both weaker (approximately between 100 and 270° C.) and stronger acid sites (approximately between 270 and 500° C.). The ratio of the number of weaker acidic sites (type 1) to stronger acidic sites (type 2) can be taken as a measure defining the relative efficiency of the catalysts for the formation of fructose from glucose.

The invention claimed is:

1. A method of isomerizing C4-C6 aldoses to their corresponding 2-ketoses, comprising the step of
   a) providing
      a first solution of one or more C5 aldoses, one or more C6 aldoses, or a mixture thereof in a first solvent, the first solvent being a C1-C3 alcohol or a combination of C1-C3 alcohol and water; or
      a second solution of one or more C4 aldoses in a second solvent, the second solvent being water or a combination of C1-C3 alcohol and water and
   b) heating the first solution or the second solution in the presence of a solid acidic zeolite catalyst containing aluminum as the only metal ("Zeolite-Al").

2. The method according to claim 1, comprising
   a) providing a first solution of one or more C5 aldoses, one or more C6 aldoses, or a mixture thereof in a first solvent, the first solvent being a C1-C3 alcohol;
   b) heating the first solution in the presence of a solid acidic zeolite catalyst containing aluminum as the only metal ("Zeolite-Al"),
   the method optionally further comprising
   c) adding water to the reaction mixture from step b) to obtain an aqueous mixture, and
   d) heating the aqueous mixture in the presence of said zeolite catalyst.

3. The method according to claim 2, wherein the alcohol solution is heated to between 60 and 140° C. for between 5 minutes and 24 hours in step b).

4. The method according to claim 2, which includes step c) and step d).

5. The method according to claim 4, wherein the aqueous mixture is heated to between 60 and 140° C. in step d).

6. The method according to claim 2 wherein heating in step b) and step d) independently are to a temperature from about 60° C. to about 120° C.

7. The method according to claim 1 which is a one-pot method.

8. The method according to claim 1 where heating is provided by thermal heating, electrical heating, steam or microwave heating.

9. The method according to claim 1, comprising
   a) providing a first solution of one or more C5 aldoses, one or more C6 aldoses, or a mixture thereof in a first solvent, the first solvent being a C1-C3 alcohol,
   b) heating the first solution in the presence of a suitable solid acidic zeolite catalyst containing aluminum as the only metal ("Zeolite-Al") to a temperature between 60 and 140° C. for between 5 minutes and 24 hours to obtain a reaction mixture,
   c) adding water to the reaction mixture to obtain an aqueous mixture,
   d) heating said aqueous mixture in the presence of a said zeolite catalyst to a temperature between 60 and 140° C. for between 5 minutes and 24 hours.

10. The method according to claim 1, wherein the C0 aldose is glucose or mannose and the corresponding ketose is fructose.

11. The method according to claim 1, wherein the C5 aldose is xylose or lyxose and the corresponding ketose is xylulose.

12. The method according to claim 1, when the first solvent is methanol, ethanol, n-propanol, or isopropanol.

13. The method according to claim 1, comprising
   a) providing a second solution of one or more C4 aldoses in a second solvent, the second solvent being water,
   b) heating the second solution in the presence of a suitable solid acidic zeolite catalyst containing aluminum as the only metal ("Zeolite-Al") to a temperature between 60 and 140° C. for between 5 minutes and 24 hours.

14. The method according to claim 13, wherein the C4 aldose is erythrose or threose and the corresponding ketose is erythrulose.

15. The method according to claim 1, wherein a suitable solid acidic zeolite catalyst is a solid zeolite with pore size above 5Å.

16. The method according to claim 1 wherein the solid zeolite catalyst is selected from the group consisting of HY catalysts and Hbeta catalysts.

17. The method according to claim 2, wherein the reaction times in step b) and in step d) independently are between 20 minutes and 24 hours.

18. The method according to claim 15, wherein the solid acidic zeolite catalyst is a solid zeolite with pore size between 6 and 12 Å.

19. The method according to claim 1, wherein the solid acidic zeolite catalyst has a Si/ratio of at least 6.

* * * * *